US008575107B2

(12) United States Patent
Kliger et al.

(10) Patent No.: US 8,575,107 B2
(45) Date of Patent: Nov. 5, 2013

(54) CLUSTERIN DERIVED PEPTIDE

(75) Inventors: Yossef Kliger, Rishon Le Zion (IL); Ofer Levy, D. N. Shimshon (IL); Itamar Borukhov, Ramat Hasharon (IL); Assaf Wool, Kiryat Ono (IL); Ehud Schreiber, Tel Aviv (IL); Anat Amir, D. N. Negev (IL); Zurit Levine, Herzeliya (IL); Zohar Tiran, Oranit (IL); Anat Oren, Tel Aviv (IL); Amir Toporik, Pardess Channa (IL)

(73) Assignee: Compugen Ltd., Tel Aviv (IL)

( * ) Notice: Subject to any disclaimer, the term of this patent is extended or adjusted under 35 U.S.C. 154(b) by 367 days.

(21) Appl. No.: 12/863,864

(22) PCT Filed: Jan. 22, 2009

(86) PCT No.: PCT/IL2009/000093
§ 371 (c)(1),
(2), (4) Date: Sep. 1, 2010

(87) PCT Pub. No.: WO2009/093246
PCT Pub. Date: Jul. 30, 2009

(65) Prior Publication Data
US 2010/0322938 A1     Dec. 23, 2010

Related U.S. Application Data

(60) Provisional application No. 61/006,564, filed on Jan. 22, 2008, provisional application No. 61/064,514, filed on Mar. 10, 2008, provisional application No. 61/136,287, filed on Aug. 25, 2008.

(51) Int. Cl.
*C07K 9/00*     (2006.01)
*A61K 38/00*     (2006.01)

(52) U.S. Cl.
USPC ............................ 514/19.2; 530/326; 530/324

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,936,691 B2* | 8/2005 | Fiscella et al. | 530/350 |
| 7,745,391 B2* | 6/2010 | Mintz et al. | 514/19.3 |
| 7,923,253 B2* | 4/2011 | Metz et al. | 436/63 |
| 2003/0191057 A1 | 10/2003 | Fogelman et al. | |
| 2006/0034852 A1 | 2/2006 | Rixon et al. | |

FOREIGN PATENT DOCUMENTS

| | | | |
|---|---|---|---|
| WO | 00/34469 | * | 6/2000 |
| WO | 00/34469 A1 | | 6/2000 |
| WO | 01/66689 | * | 9/2001 |
| WO | 2004/005934 | * | 1/2004 |
| WO | 2006/034056 A2 | | 3/2006 |
| WO | 2006/118805 A2 | | 11/2006 |
| WO | 2007/030930 A1 | | 3/2007 |

OTHER PUBLICATIONS

Miyata et al Circulation vol. 104 p. 1407 (2001).*
Palmer JBC vol. 265 p. 6617 (1990).*
Michel et al Eur. J. Biochem. vol. 229 p. 215 (1995).*
Verbrugghe, et al., "Clusterin in human gut-associated lymphoid tissue, tonsils, and adenoids: localization to M cells and follicular dendritic cells", Histochem Cell Biol, vol. 129, pp. 311-320, (2008).
Xie, et al., "Expression of Clusterin in Human Pancreatic Cancer", Pancreas, vol. 25, No. 3, pp. 234-238, (2002).
Yamanaka, et al., "A novel antisense oligonucleotide inhibiting several antiapoptotic Bcl-2 family members induces apoptosis and enhances chemosensitivity in androgen-independent human prostate cancer PC3 cells", Mol Cancer Ther, vol. 4, No. 11, pp. 1689-1698, (2005).
Hayouka, et al., "Inhibiting HIV-1 integrase by shifting its oligomerization equilibrium", PNAS, vol. 104, No. 20, pp. 8316-8321, (2007).
Zellweger, et al., "Chemosensitization of Human Renal Cell Cancer Using Antisense Oligonucleotides Targeting the Antiapoptotic Gene Clusterin", Neoplasia, vol. 3, No. 4, pp. 360-367, (2001).
Zhao, et al., "Evaluation of Combination Chemotherapy: Integration of Nonlinear Regression, Curve Shift, Isobologram, and Combination Index Analyses", Clin Cancer Res, vol. 10, pp. 7994-8004, (2004).
The International Search Report for International Application No. PCT/IL2009/000093, two pages, mailed Jun. 10, 2009.
Kliger, et al., "Conformational change blockers", FEBS Journal, vol. 275, No. Suppl. 1, p. 170, (2008).
Navab, et al., "An Oral ApoJ Peptide Renders HDL Antiinflammatory in Mice and Monkeys and Dramatically Reduces Atherosclerosis in Apolipoprotein E-Null Mice", Arterioscler Thromb Vasc Biol., vol. 25, pp. 1932-1937, (2005).
Wilson, et al., "Clusterin is a secreted mammalian chaperone", Trends in Biochemical Sciences, vol. 25, No. 3, pp. 95-98, (2000).
An, et al., "Secreted Proteome Profiling in Human RPE Cell Cultures Derived from Donors with Age Related Macular Degeneration and Age Matched Healthy Donors", Journal of Proteome Research, vol. 5, pp. 2599-2610, (2006).

(Continued)

*Primary Examiner* — Sheela J Huff
(74) *Attorney, Agent, or Firm* — Vorys, Sater, Seymour and Pease LLP; Susanne M. Hopkins

(57) ABSTRACT

Clusterin-derived peptides or homologues or derivatives thereof, pharmaceutical compositions including the same, methods of manufacturing the peptides, homologues, derivatives thereof and compositions including the same, and methods of treating conditions including administering the peptides, homologues, derivatives thereof and compositions including the same, are provided. Also provided are nucleotide sequences encoding the peptides, homologues, derivatives thereof and compositions including the same, antibodies directed to epitopes thereof and fusion proteins including the same.

6 Claims, 17 Drawing Sheets

(56) References Cited

OTHER PUBLICATIONS

Andersen, et al., "Clusterin Expression in Normal Mucosa and Colorectal Cancer", Molecular & Cellular Proteomics, vol. 6, No. 6, pp. 1039-1048, (2007).
Biroccio, et al., "Antisense Clusterin Oligodeoxynucleotides Increase the Response of HER-2 Gene Amplified Breast Cancer Cells to Trastuzumab", Journal of Cellular Physiology, vol. 204, pp. 463-469, (2005).
Boerner, et al., "Production of Antigen-Specific Human Monoclonal Antibodies from In Vitro-Primed Human Splenocytes", The Journal of Immunology, vol. 147, No. 1, pp. 86-95, (1991).
Boulares, et al., "Role of Poly(ADP-ribose) Polymerase (PARP) Cleavage in Apoptosis: Caspase 3-Resistant PARP Mutant Increases Rates of Apoptosis in Transfected Cells", The Journal of Biological Chemistry, vol. 274, No. 33, pp. 22932-22940, (1999).
Cao, et al., "Clusterin as a Therapeutic Target for Radiation Sensitization in a Lung Cancer Model", Int. J. Radiation Oncology Biol. Phys., vol. 63, No. 4, pp. 1228-1236, (2005).
Choi-Miura, et al., "Relationship Between Multifunctional Protein 'Clusterin' and Alzheimer Disease", Neurobiology of Aging, vol. 17, No. 5, pp. 717-722, (1996).
Chung, et al., "Enhanced chemosensitivity of bladder cancer cells to cisplatin by suppression of clusterin in vitro", Cancer Letters, vol. 203, pp. 155-161, (2004).
Pazos, et al., "A graphical interface for correlated mutations and other protein structure prediction methods", vol. 13, No. 3, pp. 319-321, (1997).
Fishwild, et al., "High-avidity human IgGκmonoclonal antibodies from a novel strain of minilocus transgenic mice", Nature Biotechnology, vol. 14, pp. 845-851, (1996).
Freixes, et al., "Clusterin solubility and aggregation in Creutzfeldt-Jakob disease", Acta Neuropathol, vol. 108, pp. 295-301, (2004).
Gloor, et al., "Mutual Information in Protein Multiple Sequence Alignments Reveals Two Classes of Coevolving Positions", Biochemistry, vol. 44, pp. 7156-7165, (2005).
Shackelford, et al., "Contact prediction using mutual information and neural nets", Proteins, vol. 69 (Suppl. 8), pp. 159-164, (2007).
Yin, et al., "Computational Design of Peptides That Target Transmembrane Helices", Science, vol. 315, pp. 1817-1822, (2007).
Hoogenboom, et al., "By-passing Immunisation: Human Antibodies from Synthetic Repertoires of Germline VH Gene Segments Rearranged in Vitro", J. Mol. Biol., vol. 227, pp. 381-388, (1992).
Trougakos, et al., "Regulation of clusterin/apolipoprotein J, a functional homologue to the small heat shock proteins, by oxidative stress in ageing and age-related diseases", Free Radical Research, vol. 40, No. 12, pp. 1324-1334, (2006).
Smith, et al., "Do Cells Cycle?", Proc. Nat. Acad. Sci. USA, vol. 70, No. 4, pp. 1263-1267, (1973).
Cheng, et al "Improved residue contact prediction using support vector machines and a large feature set", BMC Bioinformatics, vol. 8, p. 113 (pp. 1-9), (2007).
Izarzugaza, et al., "Assessment of intramolecular contact predictions for CASP7", Proteins, vol. 69, Suppl. 8, pp. 152-158, (2007).
Monod, et al., "On the Nature of Allosteric Transitions: A Plausible Model", J. Mol. Biol., vol. 12, pp. 88-118, (1965).
Jones, et al., "Replacing the complementarity-determining regions in a human antibody with those from a mouse", Nature, vol. 321, pp. 522-525, (1986).
Kurahashi, et al., "Expression of the secreted form of clusterin protein in renal cell carcinoma as a predictor of disease extension", BJU Int, vol. 96, No. 6, pp. 895-899, (2005).
Martin, et al., "Using information theory to search for co-evolving residues in proteins", Bioinformatics, vol. 21, No. 22, pp. 4116-4124, (2005).
Lamoyi, et al., "Preparation of F(ab')2 Fragments from Mouse IgG of Various Subclasses", Journal of Immunological Methods, vol. 56, pp. 235-243, (1983).
Larrick, et al., "PCR Amplification of Antibody Genes", METHODS: A Companion to Methods in Enzymology, vol. 2, No. 2, pp. 106-110, (1991).
Lonberg, et al., "Human Antibodies from Transgenic Mice", Intern. Rev. Immunol., vol. 13, No. 1, pp. 65-93, (1995).
Lonberg, et al., "Antigen-specific human antibodies from mice comprising four distinct genetic modifications", Nature, vol. 368, pp. 856-859, (1994).
Marks, et al., "By-Passing Immunization: Building High Affinity Human Antibodies by Chain Shuffling", Bio/Technology, vol. 10, pp. 779-783, (1992).
Marks, et al., "By-passing Immunization: Human Antibodies from V-gene Libraries Displayed on Phage", J. Mol. Biol., vol. 222, pp. 581-597, (1991).
Miyake, et al., "Therapeutic Efficacy of Adenoviral-Mediated p53 Gene Transfer Is Synergistically Enhanced by Combined Use of Antisense Oligodeoxynucleotide Targeting Clusterin Gene in a Human Bladder Cancer Model", Neoplasia, vol. 7, No. 2, pp. 171-179, (2005).
Miyake, et al., "Synergistic Chemsensitization and Inhibition of Tumor Growth and Metastasis by the Antisense Oligodeoxynucleotide Targeting Clusterin Gene in a Human Bladder Cancer Model", Clin Cancer Res, vol. 7, pp. 4245-4252, (2001).
Miyake, et al., "Synergistic Antitumor Activity by Combined Treatment with Gemcitabine and Antisense Oligodeoxynucleotide Targeting Clusterin Gene in an Intravesical Administration Model Against Human Bladder Cancer KoTCC-1 Cells", The Journal of Urology, vol. 171, pp. 2477-2481, (2004).
Miyake, et al., "Enhanced expression of the secreted form of clusterin following neoadjuvant hormonal therapy as a prognostic predictor in patients undergoing radical prostatectomy for prostate cancer", Oncology Reports, vol. 14, pp. 1371-1375, (2005).
Moretti, et al., "Clusterin Isoforms Differentially Affect Growth and Motility of Prostate Cells: Possible Implications in Prostate Tumorigenesis", Cancer Res, vol. 67, pp. 10325-10333, (2007).
Morrison, "Success in specification", Nature, vol. 368, p. 812-813, (1994).
Neuberger, "Generating high-avidity human Mabs in mice", Nature Biotechnology, vol. 14, p. 826, (1996).
Parham, "On the Fragmentation of Monoclonal IgG1, IgG2a, and IgG2b from BALB/c MICE", The Journal of Immunology, vol. 131, No. 6, pp. 2895-2902, (1983).
Park, et al., "Clusterin confers paclitaxel resistance in cervical cancer", Gynecologic Oncology, vol. 103, pp. 996-1000, (2006).
Presta, "Antibody engineering for therapeutics", Current Opinion in Structural Biology, vol. 13, pp. 519-525, (2003).
Riechmann, et al., "Reshaping human antibodies for therapy", Nature, vol. 332, pp. 323-327, (1988).
Rodriguez-Pineiro, et al., "Differential Expression of Serum Clusterin Isoforms in Colorectal Cancer", Molecular & Cellular Proteomics, vol. 5, No. 9, pp. 1647-1657, (2006).
Dunn, et al., "Mutual information without the influence of phylogeny or entropy dramatically improves residue contact prediction", vol. 24, No. 3, pp. 333-340, (2008).
Choi, et al. "Robust signals of coevolution of interacting residues in mammalian proteomes identified by phylogeny-aided structural analysis", Nature Genetics, vol. 37, No. 12, pp. 1367-1371, (2005).
Lockless, et al., "Evolutionarily Conserved Pathways of Energetic Connectivity in Protein Families", Science, vol. 286, pp. 295-299, (1999).
Schmitz, "Drug evaluation: OGX-011, a clusterin-inhibiting antisense oligonucleotide", Current Opinion in Molecular Therapeutics, vol. 8 No. 6, pp. 547-554, (2006).
Shannan, et al., "Clusterin (CLU) and Melanoma Growth: CLU is Expressed in Malignant Melanoma and 1,25-Dihydroxyvitamin D3 Modulates Expression of CLU in Melanoma Cell Lines In Vitro", Anticancer Research, vol. 26, pp. 2707-2716 (2006).
Shannan, et al., "Challenge and promise: roles for clusterin in pathogenesis, progression and therapy of cancer", Cell Death and Differentiation, vol. 13, pp. 12-19, (2006).
Silkensen, et al., "The role of clusterin in tissue injury", Biochem. Cell. Biol., vol. 72, p. 483-488, (1994).
Göbel, et al., "Correlated Mutations and Residue Contacts in Proteins", PROTEINS: Structure, Function, and Genetics, vol. 18, pp. 309-317, (1994).
Sobolev, et al., "Automated analysis of interatomic contacts in proteins", Bioinformatics, vol. 15, No. 4, pp. 327-332, (1999).

* cited by examiner

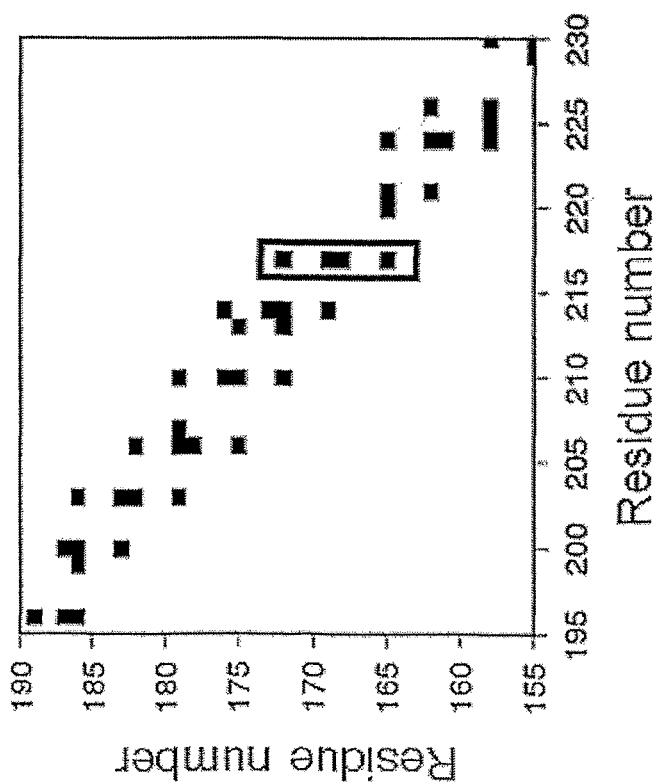
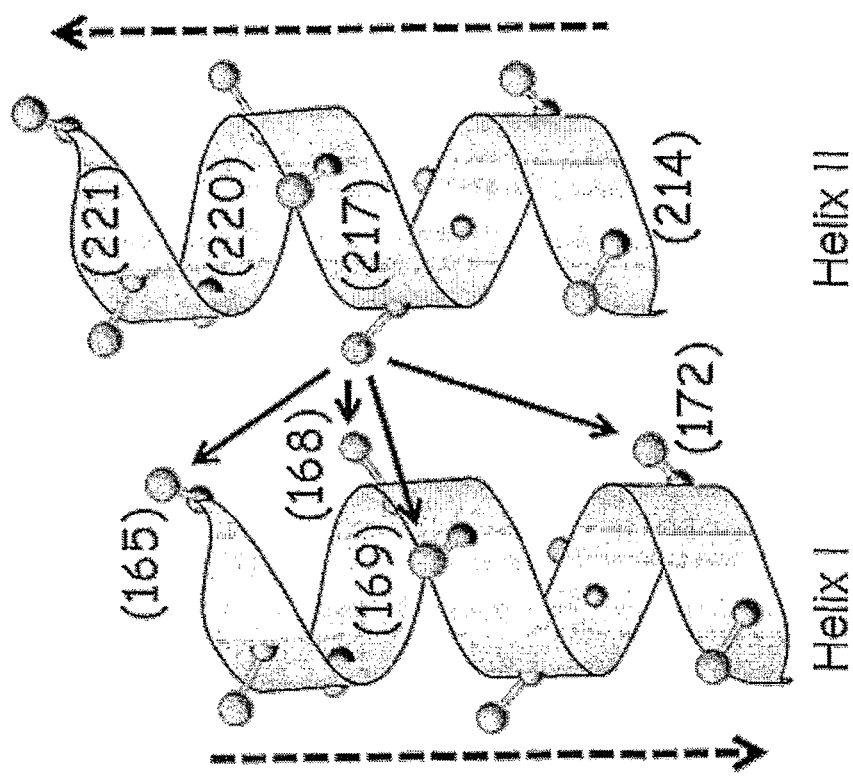
Figure 7A
Figure 7B

| | |
|---|---|
| gi\|427409077_01[Homo sapiens] | FYFWMNGDRIDSLLENDRQQT |
| gi\|126723644_01[Oryctolagus cuniculus] | FYFWINGDRIDSLLENDRQQS |
| gi\|7229152_01[Mus musculus] | FYFWMNGDRIDSLLESDRQQS |
| gi\|4461756_01[Rattus norvegicus] | FYFWMNGDRIDSLLESDRQQS |
| gi\|126352584_01[Equus caballus] | FYFWINGDRIDSLLENDRQQT |
| gi\|50979240_01[Canis familiaris] | FYFWMNGDRIDSLLENDRQQT |
| gi\|47522770_01[Sus scrofa] | FYFWINGDRIDSLMENDRQQS |
| gi\|27806907_01[Bos taurus] | FYFWINGDRIDSLMENDREQS |
| gi\|17705937_01[Coturnix coturnix japonica] | FSIWVNGERIDDLLDREQRQE |

Figure 13

CLUSTERIN DERIVED PEPTIDE

This is a National Phase Application filed under 35 U.S.C. 371 as a national stage of PCT/IL2009/000093, filed on Jan. 22, 2009, an application claiming the benefit under 35 USC 119(e) U.S. Provisional Application No. 61/006,564 filed on Jan. 22, 2008, and an application claiming the benefit under 35 USC 119(e) U.S. Provisional Application No. 61/064,514 filed on Mar. 10, 2008, and an application claiming the benefit under 35 USC 119(e) U.S. Provisional Application No. 61/136,287 filed on Aug. 25, 2008, the content of each of which is hereby incorporated by reference in its entirety.

FIELD OF THE INVENTION

This invention relates to the field of clusterin derivatives.

SEQUENCE LISTING

"The Sequence Listing submitted in text format (.txt) on Jul. 21, 2010, named 1883727_ST25.txt, (created on Wednesday, Jul. 21, 2010, 9.23 KB), is incorporated herein by reference."

BACKGROUND OF THE INVENTION

Cancer cells often develop resistance to various chemotherapy agents. One of the mechanisms that contributes to such resistance is the elevation of Clusterin in its secreted form.

Clusterin (also known as CLU, Apolipoprotein J, ApoJ, testosterone repressed prostate message-2, TRPM-2, and sulfated glycoprotein-2) is a well known multifunctional, ubiquitously expressed protein that has been implicated in various cell functions including carcinogenesis and tumor progression.

Two Clusterin protein isoforms are known to be generated in human cells: a pro-apoptotic non-glycosylated nuclear form (nCLU) and a pro-survival glycosylated secreted form (sCLU) (Moretti R M, Marelli M M, Mai S, Cariboni A, Scaltriti M, Bettuzzi S, Limonta P. *Clusterin isoforms differentially affect growth and motility of prostate cells: possible implications in prostate tumorigenesis. Cancer Res* 2007; 67(21):10325-10333; Shannan B, Seifert M, Leskov K, Willis J, Boothman D, Tilgen W, Reichrath J. *Challenge and promise: roles for clusterin in pathogenesis, progression and therapy of cancer. Cell Death Differ* 2006; 13(1):12-1).

Upregulation of sCLU appears to be a general response to molecular stress. In particular, progression towards high-grade and metastatic carcinoma is correlated with a shift from nCLU to sCLU expression (Kurahashi T, Muramaki M Yamanaka K, Hara I, Miyake H. *Expression of the secreted form of clusterin protein in renal cell carcinoma as a predictor of disease extension. BJU Int* 2005; 96(6):895-899.)

In addition, sCLU is associated with resistance to various anti-cancer treatments including chemotherapy (Park D C, Yeo S G, Shin E Y, Mok S C, Kim D H. *Clusterin confers paclitaxel resistance in cervical cancer. Gynecol Oncol* 2006; 103(3):996-1000), radiotherapy (Cao C, Shinohara E T, Li H, Niermann K J, Kim K W, Sekhar K R, Gleave M Freeman M, Lu B. *Clusterin as a therapeutic target for radiation sensitization in a lung cancer model. Int J Radiat Oncol Biol Phys* 2005; 63(4):1228-1236), hormone ablation (Miyake H, Yamanaka K, Muramaki M Kurahashi T, Gleave M, Hara I. *Enhanced expression of the secreted form of clusterin following neoadjuvant hormonal therapy as a prognostic predictor in patients undergoing radical prostatectomy for prostate cancer. Oncol Rep* 2005; 14(5):1371-1375), and specific antibodies (Biroccio A, D'Angelo C, Jansen B, Gleave M E, Zupi G. *Antisense clusterin oligodeoxynucleotides increase the response of HER-2 gene amplified breast cancer cells to Trastuzumab. J Cell Physiol* 2005; 204(2):463-469).

Antagonists of sCLU have the potential to re-sensitize chemotherapy resistant malignancies.

Schmitz G. *Drug evaluation: OGX-011, a clusterin-inhibiting antisense oligonucleotide. Curr Opin Mol Ther* 2006; 8(6):547-554 describe OGX-011, a clusterin-inhibiting antisense oligonucleotide (ASO) as a potential treatment for increasing the susceptibility of resistant solid tumors (breast, non-small-cell lung and prostate) to conventional cancer therapies.

There have further been preliminary results demonstrating potential use of siRNA-mediated clusterin down regulation for treatment of cancers, such as colorectal cancer (Andersen C L, et al., *Mol Cell Proteomics* 2007; 6(6):1039-1048; Rodriguez-Pineiro A M, et al., *Mol Cell Proteomics* 2006; 5(9): 1647-1657), melanoma (Shannan B, et al., *Anticancer Res* 2006; 26(4A):2707-2716), renal cell cancer (Zellweger T, et al., *Neoplasia* 2001; 3(4):360-367), bladder cancer (Chung J, et al., *Cancer Lett* 2004; 203(2):155-161; Miyake H, et al., *J Urol* 2004; 171(6 Pt 1):2477-2481; Miyake H, et al., *Clin Cancer Res* 2001; 7(12):4245-4252; Miyake H, et al., *Neoplasia* 2005; 7(2):171-179; Yamanaka K, et al., *Oncol Rep* 2005; 13(5):885-890) and pancreatic cancer (Xie M J, et al., *Pancreas* 2002; 25(3):234-238).

Clusterin is further involved in the epithelial-to-mesenchymal transition of carcinoma cells. WO2007/030930 describes agents (such as monoclonal antibodies), having binding-activity to clusterin, which inhibit the epithelial-to-mesenchymal transition (EMT) in carcinomas.

Furthermore, the level of clusterin is increased in the hippocampus and frontal cortex of the brains of Alzheimer's Disease patients. It is currently believed that clusterin, by binding to beta-amyloid, a protein known to aggregate in the brains of these patients, acts to link the progression of this disease to the complement system (Choi-Miura and oda, *Neurobiol. Aging,* 1996, 17, 717722).

sCLU in fact appears to be a part of the beta-amyloid complex and other complexes related to neurodegenerative disorders, and has been correlated to age-related macular degeneration (AMD) (An E, Lu X, et al., *J Proteome Res* 2006; 5(10:2599-2610), Alzheimer's Disease (AD) (Choi-Miura N H, et al., *Neurobiol Aging* 1996; 17(5):717-722), and Creutzfeldt-Jakob Disease (Freixes M, et al. *Acta Neuropathol* 2004; 108(4):295-301).

Clusterin is overexpressed in many disease states including neurodegenerative disorders, gliomas, and retinitis pigmentosa. Expression is induced in acute and chronic models of renal injury and disease, following ureter obstruction, ischemia/reperfusion, and atherosclerosis (Silkensen et al., *Biochem. Cell. Biol.,* 1994, 72, 483-488).

Clusterin is also expressed in M cells (microfold cells) and follicular dendritic cells at inductive sites of human mucosa-associated lymphoid tissue (Waelput W et al., *Histochem Cell Biol.* 2007 Dec. 21).

Clusterin has further been implicated in various physiological processes and physiological disturbance states including ageing, cancer progression, vascular damage, diabetes, kidney and neuron degeneration (Ioannis P. Trougakos & Efstathios S. Gonos; *Free Radical Research,* December 2006; 40(12): 1324-1334). Although unrelated in their etiology and clinical manifestation, these diseases represent states of increased oxidative stress, which in turn, promote amorphous aggregation of target proteins, increased genomic instability and high rates of cellular death. Among the various properties attributed to clusterin so far, those mostly investigated and invariably appreciated are its small heat shock proteins-like chaperone activity and its involvement in cell death regulation, which are both directly correlated to the main features of oxidant injury. Moreover, the presence of both a heat shock transcription factor-1 and an activator protein-1 element in the clusterin gene promoter indicates that the clusterin gene can be an extremely sensitive biosensor to reactive oxygen species.

To date, there are no known therapeutic agents which effectively inhibit the synthesis of clusterin. Investigative strategies aimed at modulating clusterin function have involved the use of antibodies, antisense oligonucleotides and chemical inhibitors. As in all technologies at all times, these agents can be improved upon and there remains a need for additional agents capable of effectively inhibiting clusterin.

SUMMARY OF THE INVENTION

The subject invention now provides novel peptides corresponding to segments of sCLU, homologs thereof, orthologs thereof, derivatives thereof, antibodies directed thereto, fusion proteins comprising them, all of which have a therapeutic value for a wide range of conditions, disorders and diseases.

In one aspect of this invention the conditions, disorders and diseases are conditions, disorders and diseases where induction of tumor growth arrest can be of therapeutic value.

The subject invention thus provides a peptide consisting essentially of an amino acid sequence FYFWMNGDRIDSL-LENDRQQT (CGEN-CL1) [SEQ ID NO: 1] or a homolog or a derivative thereof.

The subject invention further provides a homolog of a CGEN-CL1 peptide of the invention consisting essentially of an amino acid sequence LEEFLNQSSPFYFWMNGDRID-SLLENDRQQTHMLDVMQDHF [SEQ ID NO: 3].

The subject invention further provides a peptide consisting essentially of an amino acid sequence as set forth in any one of SEQ ID NOs: 6-13.

The subject invention further provides a peptide consisting essentially of an amino acid sequence corresponding to a partner helix of a peptide of the invention.

The subject invention further provides a partner helix peptide consisting essentially of an amino acid sequence RLTRKYNELLKSYQWKMLNTSS (SEQ ID NO: 5) or a homolog or a derivative thereof.

The subject invention further provides a partner helix peptide consisting essentially of an amino acid sequence ELDESLQVAERLTRKYNELLKSYQWK-MLNTSSLLEQLNEQFN (SEQ ID NO: 15) or a homolog or a derivative thereof.

The subject invention further provides a partner helix peptide consisting essentially of an amino acid sequence NNPSQAKLRRRELDESLQVAER-LTRKYNELLKSYQWKMLNTSSLLEQLNEQFN WVSR-LANLTQ (SEQ ID NO: 16) or a homolog or a derivative thereof.

The subject invention also provides an antibody that selectively binds to an epitope in a peptide as set forth in any one of SEQ ID NOs: 1, 3 and SEQ ID NOs: 5-13, 15 and 16.

The subject invention further provides a conjugate or fusion protein comprising a peptide of the invention as set forth in any one of SEQ ID NOs: 1, 3 and SEQ ID NOs: 5-13, 15 and 16.

The subject invention further provides a pharmaceutical composition comprising a peptide of the invention or a homolog thereof or a derivative thereof, an antibody of the invention or a fusion protein of the invention and a pharmaceutically acceptable carrier. The subject invention further envisages a peptide of the invention or a homolog or a derivative thereof, an antibody of the invention or a fusion protein of the invention for use in therapy and further envisages a use of the peptide of the invention or a homolog or a derivative thereof, an antibody of the invention or a fusion protein of the invention for the manufacture of a medicament.

The subject invention further provides a method of treating cancer comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of inhibiting epithelial-to mesenchymal transition in carcinoma cells comprising administering a pharmaceutically effective amount of a peptide of the invention or a homolog thereof or a derivative thereof, an antibody of the invention or a fusion protein of the invention and a pharmaceutically acceptable carrier to a subject in need thereof.

The subject invention further provides a method of treating a neurodegenerative disease comprising administering a pharmaceutically effective amount of a peptide of the invention or a homolog thereof or a derivative thereof, an antibody of the invention or a fusion protein of the invention and a pharmaceutically acceptable carrier to a subject in need thereof.

The subject invention further provides a method of treating a disease related to inflammation of the gastrointestinal tract comprising administering a pharmaceutically effective amount of a peptide of the invention or a homolog thereof or a derivative thereof, an antibody of the invention or a fusion protein of the invention and a pharmaceutically acceptable carrier to a subject in need thereof.

The subject invention further provides a method of treating a pathological disorder characterized by increased oxidative stress comprising administering a pharmaceutically effective amount of a peptide of the invention or a homolog thereof or a derivative thereof, an antibody of the invention or a fusion protein of the invention and a pharmaceutically acceptable carrier to a subject in need thereof.

The subject invention also provides a nucleotide sequence encoding a peptide of the invention or a homolog thereof.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1A demonstrates absolute absorbance values (OD) of MCF-7 cells treated with various doses of CGEN-CL1. FIG. 1B demonstrates absolute absorbance values of PC3 cells treated with various doses of paclitaxel (taxol). FIG. 1C and FIG. 1D respectively demonstrate the absolute absorbance values and the relative growth normalized to non-treated cells of A549 cells, treated with various concentrations of CGEN-CL1.

FIG. 1E and FIG. 1F respectively demonstrate the absolute absorbance values and the relative growth normalized to non-treated cells of HT29 cells, treated with various concentrations of CGEN-CL1.

FIG. 1G and FIG. 1H respectively demonstrate the absolute absorbance values or the relative growth normalized to non-treated cells of SK-MEL cells, treated with various concentrations of CGEN-CL1.

FIG. 2A presents untreated PC3 cells; FIG. 2B presents cells treated with 300 nM of CGEN-CL1 [SEQ ID NO:1]; and FIG. 2C presents cells treated with 1 µM of CGEN-CL1 [SEQ ID NO:1]. FIG. 2D presents graphically the percentage of cells in the different stages of cell cycle. P2, P3, P4, P5 are arbitrary symbols defining different gating areas under FACS histogram. P2 corresponds to the fraction of cells at Sub G0/G1 stage, P3 corresponds to the fraction of cells at G0/G1 stage, P3 corresponds to the fraction of cells at S stage, P4 corresponds to the fraction of cells at G2/M stage. Sub G0/G1, G0/G1, S and G2/M cell cycle stages are described for example in J. A. Smith and L. Martin, 1973, *PNAS* 70 (4): 1263-1267.

FIGS. 7A-7D demonstrate identification of helix-helix interactions using a unique computerized method. FIGS. 7A and 7B demonstrate a known example for a protein (BAG-1, Protein Data Bank ID 1hx1 (chain B)) that comprises two helices that interact with each other in an anti-parallel manner. FIG. 7A presents the residue-residue contact map, corresponding to the two anti-parallel helices taken from BAG-1; FIG. 7B demonstrates a schematic view of two helices interacting through their adjacent faces; FIG. 7C demonstrates a subset of the residue-residue contact map for clusterin (residues 100-400) as predicted by SVMcon (J. Cheng, P. Baldi, *BMC Bioinformatics* 8, 113 (2007); FIG. 7D shows a map of scores based on the Fourier transform of the correlated mutation signal of clusterin FIGS. 8A-8B present in Silico detection of a helix-helix interaction in clusterin.

FIG. 10A presents a schematic diagram of a conformational change in a protein, and FIG. 10B shows the blockage of the conformational change in a protein by a peptide corresponding to one of the helices. FIG. 10C demonstrates that according to this potential mechanism of action, pre-incubation of the blocking peptide CGEN-CL1 (SEQ ID NO: 1) with a peptide corresponding to a partner helix (SEQ ID NO:5) abolishes the inhibitory effect of CGEN-CL1 (SEQ ID NO: 1).

FIG. 13: shows a multiple alignment comparison of the sequence of CGEN-CL1 (SEQ ID NO:1) and the orthologous sequences derived from >gi|126723644_0|*[Oryctolagus cuniculus]*, >gi|126352584_0|*[Equus caballus]*, >gi|47522770_0|*[Sus scrofa]*, >gi|50979240_0|*[Canis familiaris]*, >gi|461756_0|*[Rattus norvegicus]*, >gi|27806907_0|*[Bos taurus]*, >gi|1705937_0|*[Coturnix coturnix japonica]*, >gi|729152_0|*[Mus musculus]*, corresponding to SEQ ID NOs: 6-13.

DETAILED DESCRIPTION OF THE INVENTION

Figure 1A:
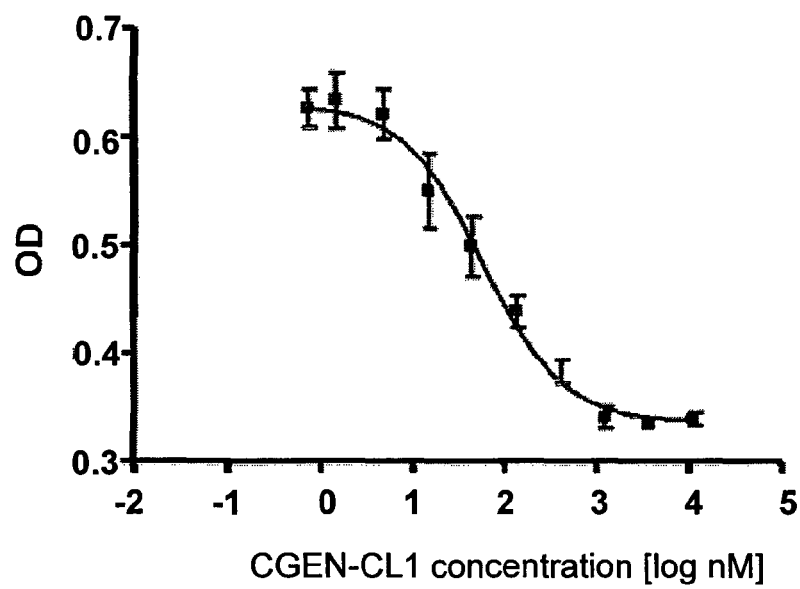
FIGS. 1A-1H demonstrate the effect of CGEN-CL1 on cell growth of various cancer cell lines as revealed by MTT assay.

The subject invention provides a peptide consisting essentially of an amino acid sequence FYFWMNGDRIDSLLEN-DRQQT (CGEN-CL1) [SEQ ID NO:1] or a homolog thereof or a derivative thereof. CGEN-CL1 corresponds to amino acid residues 150-170 of the clusterin isoform 2 protein sequence (GenBank Accession number:gi|42740907).

The term "homolog" relating to a peptide of the invention as used herein should be understood to encompass a peptide which has substantially the same amino acid sequence and substantially the same biological activity as CGEN-CL1. Thus, a homolog may differ from the CGEN-CL1 peptide by the addition, deletion or substitution of one or more amino acid residues, provided that the resulting peptide retains the biological activity of CGEN-CL1. Persons skilled in the art can readily determine which amino acid residues may be added, deleted or substituted (including with which amino acids such substitutions may be made) using established well known procedures. Examples of homologs of CGEN-CL1 are deletion homologs containing less than all the amino acid residues of CGEN-CL1, substitution homologs wherein one or more amino acid residues specified are replaced by other amino acid residues (or by D-amino acids, or by non-natural amino acids) and addition homologs wherein one or more amino acid residues are added to a terminal or medial portion of CGEN-CL1, all of which share the biological activity of CGEN-CL1.

In one embodiment, a homolog of a peptide of the invention is LEEFLNQSSPFYFWMNGDRIDSLLEN-DRQQTHMLDVMQDHF [SEQ ID NO: 3] which corresponds to amino acid residues 140-180 of the clusterin isoform 2 protein sequence (GenBank Accession number: gi|42740907).

The term "homolog" relating to a peptide of the invention as used herein should also be understood to encompass an ortholog. The term "ortholog" should be understood to encompass a peptide derived from a non-human origin which has substantially the same amino acid sequence and substantially the same biological activity as CGEN-CL1.

The subject invention thus provides a peptide being an ortholog of CGEN-CL1 [SEQ ID NO: 1], consisting essentially of an amino acid sequence as depicted in any one of SEQ ID NOs: 6-13, or a derivative thereof.

The term "partner helix (peptide)" as used herein should be understood to encompass a peptide corresponding to an alpha helix within the parent clusterin protein, which physically interacts with a peptide of the invention.

The subject invention thus further provides a peptide consisting essentially of an amino acid sequence corresponding to a partner helix of a peptide of the invention or a homolog or a derivative thereof.

The subject invention provides a peptide consisting essentially of an amino acid sequence corresponding to a partner helix of a peptide having an amino acid sequence as depicted in SEQ ID NO: 1.

The subject invention further provides a peptide consisting essentially of an amino acid sequence RLTRKYNELLKSYQWKMLNTSS (SEQ ID NO:5), corresponding to a partner helix of CGEN-CL1 (SEQ ID NO: 1). This peptide SEQ ID NO:5 corresponds to amino acid residues 336-357 of the clusterin protein sequence (GenBank Accession number: gi|42740907_0|*[Homo sapiens]* |CLUS_HUMAN, SEQ ID NO: 14).

The subject invention further provides a peptide consisting essentially of an amino acid sequence ELDESLQVAERLTRKYNELLKSYQWKMLNTSSLLEQLNEQFN (SEQ ID NO: 15), corresponding to a partner helix of CGEN-CL1 (SEQ ID NO: 1). This peptide SEQ ID NO:15 corresponds to amino acid residues 326-367 of the clusterin protein sequence (GenBank Accession number: gi|427409_0|*[Homo sapiens]* |CLUS_HUMAN, SEQ ID NO: 14).

The subject invention further provides a peptide consisting essentially of an amino acid sequence NNPSQAKLRRELDESLQVAERLTRKYNELLKSYQWKMLNTSSLLEQLNEQFN WVSRLANLTQ (SEQ ID NO: 16), corresponding to a partner helix of CGEN-CL1 (SEQ ID NO: 1). This peptide SEQ ID NO:16 corresponds to amino acid residues 316-377 of the clusterin protein sequence (GenBank Accession number: gi|42740907_0|*[Homo sapiens]* |CLUS_HUMAN, SEQ ID NO: 14).

The subject invention further provides an antibody that selectively binds to an epitope within a peptide of the invention. In one embodiment, said epitope is located in a peptide of the invention, as depicted in any one of SEQ ID NOs: 1, 3. In another embodiment, said epitope is located in a peptide of the invention, depicted in any one of SEQ ID NOs:6-13. In yet another embodiment, said epitope is located in a peptide of the invention, depicted in any one of SEQ ID NOs: 5, 15, 16.

The subject invention further provides an antibody that selectively binds to an epitope in a helix-helix structure derived from the interaction of a peptide of the invention with a corresponding partner helix.

The subject invention further provides a conjugate or fusion protein comprising a peptide of the invention as set forth in any one of SEQ ID NOs: 1, 3 and SEQ ID NOs: 5-13, 15 and 16.

In one aspect of the invention, a peptide of the invention induces tumor growth arrest. In another embodiment, a peptide of the invention enhances the cytostatic activity of chemotherapeutic agents such as, but not limited to paclitaxel, hence enabling treatment with reduced doses of chemotherapy. The names paclitaxel, taxol and docetaxel are used interchangeably herein.

All amino acid sequences and nucleic acid sequences shown herein as embodiments of the present invention relate to their isolated form.

Non-natural amino acids are known to those skilled in the art of chemical synthesis and peptide chemistry. Non-limiting examples of non-natural amino acids (each one in L- or D-configuration) are azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl)alanin and those listed in Table 1 below.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| | | L-N-methylasparagine | Nmasn |
| aminocyclopropane-carboxylate | Cpro | L-N-methylaspartic acid | Nmasp |
| | | L-N-methylcysteine | Nmcys |
| aminoisobutyric acid | Aib | L-N-methylglutamine | Nmgln |
| aminonorbornyl-carboxylate | Norb | L-N-methylglutamic acid | Nmglu |
| | | L-N-methylhistidine | Nmhis |
| cyclohexylalanine | Chexa | L-N-methylisolleucine | Nmile |
| cyclopentylalanine | Cpen | L-N-methylleucine | Nmleu |
| D-alanine | Dal | L-N-methyllysine | Nmlys |
| D-arginine | Darg | L-N-methylmethionine | Nmmet |
| D-aspartic acid | Dasp | L-N-methylnorleucine | Nmnle |
| D-cysteine | Dcys | L-N-methylnorvaline | Nmnva |
| D-glutamine | Dgln | L-N-methylornithine | Nmorn |
| D-glutamic acid | Dglu | L-N-methylphenylalanine | Nmphe |
| D-histidine | Dhis | L-N-methylproline | Nmpro |
| D-isoleucine | Dile | L-N-methylserine | Nmser |
| D-leucine | Dleu | L-N-methylthreonine | Nmthr |
| D-lysine | Dlys | L-N-methyltryptophan | Nmtrp |
| D-methionine | Dmet | L-N-methyltyrosine | Nmtyr |
| D-ornithine | Dorn | L-N-methylvaline | Nmval |
| D-phenylalanine | Dphe | L-N-methylethylglycine | Nmetg |
| D-proline | Dpro | L-N-methyl-t-butylglycine | Nmtbug |
| D-serine | Dser | | |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | | |
| D-α-methylalanine | Dmala | α-methyl-γ-aminobutyrate | Mgabu |
| D-α-methylarginine | Dmarg | α-methylcyclohexylalanine | Mchexa |
| D-α-methylasparagine | Dmasn | | |
| D-α-methylaspartate | Dmasp | α-methylcyclopentylalanine | Mcpen |
| D-α-methylcysteine | Dmcys | | |
| D-α-methylglutamine | Dmgln | α-methyl-α-napthylalanine | Manap |
| D-α-methylhistidine | Dmhis | | |
| D-α-methylisoleucine | Dmile | α-methylpenicillamine | Mpen |
| D-α-methylleucine | Dmleu | N-(4-aminobutyl)glycine | Nglu |
| D-α-methyllysine | Dmlys | N-(2-aminoethyl)glycine | Naeg |
| D-α-methylmethionine | Dmmet | N-(3-aminopropyl)glycine | Norn |
| D-α-methylornithine | Dmorn | N-amino-α-methylbutyrate | Nmaabu |
| D-α-methylphenylalanine | Dmphe | | |
| D-α-methylproline | Dmpro | α-napthylalanine | Anap |
| D-α-methylserine | Dmser | N-benzylglycine | Nphe |
| D-α-methylthreonine | Dmthr | N-(2-carbamylethyl)glycine | Ngln |
| D-α-methyltryptophan | Dmtrp | N-(carbamylmethyl)glycine | Nasn |
| D-α-methyltyrosine | Dmty | | |
| D-α-methylvaline | Dmval | N-(2-carboxyethyl)glycine | Nglu |
| D-α-methylalnine | Dnmala | | |
| D-α-methylarginine | Dnmarg | N-(carboxymethyl)glycine | Nasp |
| D-α-methylasparagine | Dnmasn | N-cyclobutylglycine | Ncbut |
| D-α-methylasparatate | Dnmasp | N-cycloheptylglycine | Nchep |
| D-α-methylcysteine | Dnmcys | N-cyclohexylglycine | Nchex |
| D-N-methylleucine | Dnmleu | N-cyclodecylglycine | Ncdec |
| D-N-methyllysine | Dnmlys | N-cyclododecylglycine | Ncdod |

TABLE 1-continued

| Non-conventional amino acid | Code | Non-conventional amino acid | Code |
|---|---|---|---|
| N-methyl-cyclohexylalanine | Nmchexa | N-cyclooctylglycine | Ncoct |
| | | N-cyclopropylglycine | Ncpro |
| D-N-methylornithine | Dnmorn | N-cycloundecylglycine | Ncund |
| N-methylglycine | Nala | N-(2,2-diphenylethyl)glycine | Nbhm |
| N-methylamino-isobutyrate | Nmaib | | |
| | | N-(3,3-diphenylpropyl)glycine | Nbhe |
| N-(1-methylpropyl)glycine | Nile | | |
| | | N-(3-indolylyethyl) glycine | Nhtrp |
| N-(2-methylpropyl)glycine | Nile | | |
| | | N-methyl-γ-aminobutyrate | Nmgabu |
| N-(2-methylpropyl)glycine | Nleu | | |
| | | D-N-methylmethionine | Dnmmet |
| D-N-methyltryptophan | Dnmtrp | N-methylcyclopentylalanine | Nmcpen |
| D-N-methyltyrosine | Dnmtyr | | |
| D-N-methylvaline | Dnmval | D-N-methylphenylalanine | Dnmphe |
| γ-aminobutyric acid | Gabu | D-N-methylproline | Dnmpro |
| L-t-butylglycine | Tbug | D-N-methylserine | Dnmser |
| L-ethylglycine | Etg | D-N-methylserine | Dnmser |
| L-homophenylalanine | Hphe | D-N-methylthreonine | Dnmthr |
| L-α-methylarginine | Marg | N-(1-methylethyl)glycine | Nval |
| L-α-methylaspartate | Masp | N-methyla-napthylalanine | Nmanap |
| L-α-methylcysteine | Mcys | N-methylpenicillamine | Nmpen |
| L-α-methylglutamine | Mgln | N-(p-hydroxyphenyl)glycine | Nhtyr |
| L-α-methylhistidine | Mhis | | |
| L-α-methylisoleucine | Mile | N-(thiomethyl)glycine | Ncys |
| D-N-methylglutamine | Dnmgln | penicillamine | Pen |
| D-N-methylglutamate | Dnmglu | L-α-methylalanine | Mala |
| D-N-methylhistidine | Dnmhis | L-α-methylasparagine | Masn |
| D-N-methylisoleucine | Dnmile | L-α-methyl-t-butylglycine | Mtbug |
| D-N-methylleucine | Dnmleu | L-methylethylglycine | Metg |
| D-N-methyllysine | Dnmlys | L-α-methylglutamate | Mglu |
| N-methylcyclohexylalanine | Nmchexa | L-α-methylhomophenylalanine | Mhphe |
| D-N-methylornithine | Dnmorn | N-(2-methylthioethyl)glycine | Nmet |
| N-methylglycine | Nala | | |
| N-methylamino-isobutyrate | Nmaib | N-(3-guanidinopropyl)glycine | Narg |
| N-(1-methylpropyl)glycine | Nile | N-(1-hydroxyethyl)glycine | Nthr |
| N-(2-methylpropyl)glycine | Nleu | N-(hydroxyethyl)glycine | Nser |
| | | N-(imidazolylethyl)glycine | Nhis |
| D-N-methyltryptophan | Dnmtrp | | |
| D-N-methyltyrosine | Dnmtyr | N-(3-indolylyethyl)glycine | Nhtrp |
| D-N-methylvaline | Dnmval | | |
| γ-aminobutyric acid | Gabu | N-methyl-γ-aminobutyrate | Nmgabu |
| L-t-butylglycine | Tbug | | |
| L-ethylglycine | Etg | D-N-methylmethionine | Dnmmet |
| L-homophenylalanine | Hphe | N-methylcyclopentylalanine | Nmcpen |
| L-α-methylarginine | Marg | | |
| L-α-methylaspartate | Masp | D-N-methylphenylalanine | Dnmphe |
| L-α-methylcysteine | Mcys | D-N-methylproline | Dnmpro |
| L-α-methylglutamine | Mgln | D-N-methylserine | Dnmser |
| L-α-methylhistidine | Mhis | D-N-methylthreonine | Dnmthr |
| L-α-methylisoleucine | Mile | N-(1-methylethyl)glycine | Nval |
| L-α-methylleucine | Mleu | N-methyla-napthylalanine | Nmanap |
| L-α-methylmethionine | Mmet | N-methylpenicillamine | Nmpen |
| L-α-methylnorvaline | Mnva | N-(p-hydroxyphenyl)glycine | Nhtyr |
| L-α-methylphenylalanine | Mphe | | |
| | | N-(thiomethyl)glycine | Ncys |
| L-α-methylserine | mser | penicillamine | Pen |
| L-α-methylvaline | Mtrp | L-α-methylalanine | Mala |
| L-α-methylleucine | Mval | L-α-methylasparagine | Masn |
| | Nnbhm | L-α-methyl-t-butylglycine | Mtbug |
| N-(N-(2,2-diphenylethyl) carbamylmethyl-glycine | Nnbhm | L-methylethylglycine | Metg |
| | | L-α-methylglutamate | Mglu |
| | | L-α-methylhomophenylalanine | Mhphe |
| 1-carboxy-1-(2,2-diphenyl ethyl-amino)cyclopropane | Nmbc | N-(2-methylthioethyl)glycine | Nmet |
| | | L-α-methyllysine | Mlys |
| | | L-α-methylnorleucine | Mnle |
| | | L-α-methylornithine | Morn |
| | | L-α-methylproline | Mpro |
| | | L-α-methylthreonine | Mthr |
| | | L-α-methyltyrosine | Mtyr |
| | | L-N-methylhomophenylalanine | Nmhphe |

TABLE 1-continued

| Non-conventional amino acid | Code | Non-conventional amino acid | Code |
|---|---|---|---|
| | | N-(N-(3,3-diphenylpropyl) carbamylmethyl(1)glycine | Nnbhe |

The term "derivative" relating to a peptide of the invention should be understood to encompass a peptide which has substantially the same amino acid sequence and substantially the same biological activity as CGEN-CL1. Thus, a derivative may differ from the CGEN-CL1 peptide by a modification, such as but not limited to glycosylation, amidation, acetylation, alkylation, alkenylation, alkynylation, phosphorylation, sulphorization, hydroxylation, hydrogenation, cyclization and so forth. Thus, a derivative of a peptide of the invention may differ from the CGEN-CL1 peptide by a modification on one or more amino acid residues, provided that the resulting peptide retains the biological activity of CGEN-CL1. Persons skilled in the art can readily determine which amino acid residues may be modified using established well known procedures. In one embodiment, a peptide of the invention is amidated at its C-terminus and acetylated at its N-terminus.

"A peptide with substantially the same amino acid sequence as CGEN-CL1" as used herein should be understood to encompass a synthetic peptide which has at least 5, preferably at least 8 and at most 41 amino acids, which correspond to a sequential fragment of amino acids 140-180 of the clusterin isoform 2 protein sequence (GenBank Accession number: gi|42740907)[SEQ ID NO:3].

A peptide with substantially the same biological activity as CGEN-CL1 as used herein should be understood to encompass a peptide which has at least 80% of the biological activity of CGEN-CL1.

A peptide of the invention may be prepared synthetically (e.g. on a solid support by solid phase peptide synthesis or in solution) or by recombinant means (in bacteria, yeast, fungi, insect, vertebrate or mammalian cells) by methods well known to those skilled in the art.

In one embodiment, a peptide of the invention may be synthesized such that one or more of the bonds which link the amino acid residues of the peptide, are non-peptide bonds.

In another embodiment, a peptide of the invention may be synthesized with additional chemical groups, such that, for example, the stability, bioavailability, and/or inhibitory activity of the peptide is modified. For example, an acetyl group may be placed at the amino termini of a peptide of the invention. Additionally or alternatively, an amido group may be added to the carboxy termini of a peptide of the invention.

In yet another embodiment, a peptide of the invention may be synthesized with an altered steric configuration. For example, the D-isomer of one or more of the amino acid residues of a peptide of the invention may be used, rather than the usual L-isomer.

In yet a further embodiment, at least one of the amino acid residues of a peptide of the invention may be substituted by any one of the well known non-naturally occurring amino acid residues, selected from, but not limited to azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl)alanin and those from Table 1 herein.

In another embodiment, a peptide of the invention may have a non-peptide macromolecular carrier group covalently attached to its amino and/or carboxy terminus. Non-limiting examples of such macromolecular carrier groups are lipid-fatty acid conjugates, polyethylene glycol, and carbohydrates.

The subject invention further provides a pharmaceutical composition comprising a peptide of the invention or a homolog or a derivative thereof. The subject invention also provides a pharmaceutical composition comprising an antibody of the invention. The subject invention additionally provides a pharmaceutical composition comprising a fusion protein of the invention.

Suitable routes of administration of a peptide or a pharmaceutical composition of the subject invention are oral, rectal, nasal, topical (including transdermal, buccal and sublingual), vaginal or parenteral (including subcutaneous, intramuscular, intravenous and intradermal) administration or administration via an implant. In a specific embodiment, a peptide or a pharmaceutical composition of the invention can be administered intravenously.

The exact dose and regimen of administration of a peptide or pharmaceutical composition of the invention will necessarily be dependent upon the therapeutic effect to be achieved (e.g. treatment of cancer) and may vary with the particular peptide, the route of administration, and the age and condition of the individual subject to whom the medicament is to be administered.

A dosage for humans is likely to contain 1-1000 µg per kg body weight per day. The desired dose may be presented as one dose or as multiple sub-doses administered at appropriate intervals.

The present invention thus also relates to a pharmaceutical composition comprising a peptide of the subject invention or a homolog or derivative thereof (or comprising an antibody thereto or comprising a fusion protein comprising a peptide of the invention) in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association a peptide of the invention with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as herein described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The subject invention further provides a use of a peptide of the invention or a homolog or derivative thereof for the manufacture of a medicament. The subject invention also provides an antibody of the invention for the manufacture of a medicament. The subject invention additionally provides a fusion protein of the invention for the manufacture of a medicament. In one embodiment, the medicament is for the treatment of a cancer. In another embodiment, the medicament is for inhibition of epithelial-to-mesenchymal transition of carcinoma cells. In another embodiment, the medicament is for treating a neurodegenerative disease. In yet another embodiment, the medicament is for the treatment of a disease related to inflammation of the gastrointestinal tract. In yet another embodiment, the medicament is for the treatment of a pathological disorder characterized by increased oxidative stress.

The term "cancer" as used herein should be understood to encompass any neoplastic disease (whether invasive or metastatic) which is characterized by abnormal and uncontrolled cell division causing malignant growth or tumor. Non-limiting examples of cancer which may be treated with a peptide of the invention are breast cancer (e.g. breast carcinoma), cervical cancer, ovary cancer (ovary carcinoma), endometrial cancer, melanoma, bladder cancer (bladder carcinoma), lung cancer (e.g. adenocarcinoma and including non-small cell lung cancer), pancreatic cancer (e.g. pancreatic carcinoma such as, for example exocrine pancreatic carcinoma), colon cancer (e.g. colorectal carcinoma, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemia (for example, acute myelogenous leukemia (AML)), thyroid follicular cancer, myelodysplastic syndrome (MDS), tumors of mesenchymal origin (e.g. fibrosarcomas and rhabdomyosarcomas), melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, and epidermal carcinoma. In one embodiment, the cancer is selected from the group consisting of breast cancer, prostate cancer, lung cancer, colorectal cancer, melanoma, renal cancer, bladder cancer and pancreatic cancer. In a specific embodiment, the cancer is breast cancer. In another specific embodiment, the cancer is lung cancer. In yet another specific embodiment, the cancer is prostate cancer. In yet another specific embodiment, the cancer is colorectal cancer. In yet another specific embodiment, the cancer is melanoma.

The term "neurodegenerative disease" as used herein should be understood to encompass any neurodegenerative disease such as, but not limited to, age-related macular degeneration, Creutzfeldt-Jakob disease, Alzheimer's Disease, radiotherapy induced dementia, axon injury, acute cortical spreading depression, alpha-synucleinopathies, brain ischemia, Huntington's disease, permanent focal cerebral ischemia, peripheral nerve regeneration, post-status epilepticus model, spinal cord injury, sporadic amyotrophic lateralsclerosis and transmissible spongiform encephalopathy.

The term "disease related to inflammation of the gastrointestinal tract" as used herein should be understood to encompass any inflammatory disease or condition of the gastrointestinal tract, such as, but not limited to, Crohn's disease, Ulcerative colitis, Celiac disease, inflammatory bowel disease, enteritis (inflammation of the small intestine), gastritis (stomach), gastroenteritis (stomach and small intestine), colitis (large intestine), enterocolitis (large and small intestine), Cholecystitis, Pancreatitis, Irritable bowel syndrome, Caecitis, Cirrhosis and so forth.

The term "pathological disorder characterized by increased oxidative stress" as used herein should be understood to encompass any disease, disorder or condition characterized by increased oxidative stress including, but not limited to, ageing, cardiovascular disease, chronic leg ulcers, diabetes mellitus, eye disorders, kidney degeneration, myofibrillar myopathis, pancreatic disorders, systemic lupus erythematous (SLE) and urinary tract obstruction.

The term "cardiovascular disease" as used herein should be understood to encompass any cardiovascular disease, disorder or condition including, but not limited to, atherosclerotic aorta, myocardial infraction, myocarditis and vascular injury.

The term "eye disorder" as used herein should be understood to encompass any eye disease, disorder or condition including, but not limited to, ocular surface disease, pseudoexfoliation syndrome and retinal degeneration.

The term "kidney degeneration disorder" as used herein should be understood to encompass any kidney disease, disorder or condition including, but not limited to, cystic kidney disease, hydronephrotic neonatal kidney, obstructive nephropathy and renal ischemia-reperfusion.

The term "pancreatic disorder" as used herein should be understood to encompass any pancreatic disease disorder or condition including, but not limited to, pancreatitis and pancreatic acinar cell injuries.

The subject invention thus provides a peptide of the invention or a homolog or a derivative thereof for use in therapy. The subject invention also provides an antibody of the invention for use in therapy. The subject invention additionally provides a fusion protein of the invention for use in therapy.

In one embodiment, the therapy is for the treatment of a neurodegenerative disease. In a specific embodiment, the therapy is for the treatment of a neurodegenerative disease selected from the group consisting of Alzheimer's Disease, age-related macular degeneration, Creutzfeldt-Jakob disease, radiotherapy induced dementia, axon injury, acute cortical spreading depression, alpha-synucleinopathies, brain ischemia, Huntington's disease, permanent focal cerebral ischemia, peripheral nerve regeneration, post-status epilepticus model, spinal cord injury, sporadic amyotrophic lateralsclerosis and transmissible spongiform encephalopathy.

In another embodiment, the therapy is for the treatment of cancer. In a specific embodiment, the therapy is for the treatment of cancer selected from the group consisting of breast cancer, prostate cancer, lung cancer, colorectal cancer, melanoma, renal cancer, bladder cancer and pancreatic cancer. In another specific embodiment, the cancer is breast cancer. In yet another specific embodiment, the cancer is lung cancer. In yet another specific embodiment, the cancer is prostate cancer. In yet another specific embodiment, the cancer is colorectal cancer. In yet another specific embodiment, the cancer is melanoma. In one embodiment, the cancer is invasive. In another embodiment, the cancer is metastatic. In another embodiment, the therapy is for inhibition of epithelial-to-mesenchymal transition of carcinoma cells.

In yet another embodiment, the therapy is for the treatment of a disease related to inflammation of the gastrointestinal tract. In a specific embodiment, the therapy is for the treatment of a disease related to inflammation of the gastrointestinal tract selected from the group consisting of Crohn's disease, Ulcerative colitis, Celiac disease, inflammatory bowel disease, enteritis, gastritis, gastroenteritis, colitis, enterocolitis, Cholecystitis, Pancreatitis, Irritable bowel syndrome, Caecitis, and Cirrhosis.

In yet another embodiment, the therapy is for the treatment of a pathological disorder characterized by increased oxidative stress. In a specific embodiment, the therapy is for the treatment of a pathological disorder characterized by increased oxidative stress selected from the group consisting of ageing, cardiovascular disease, atherosclerotic aorta, myocardial infraction, myocarditis, vascular injury, chronic leg ulcers, diabetes mellitus, eye disorders, ocular surface disease, pseudoexfoliation syndrome, retinal degeneration, kidney degeneration, cystic kidney disease, hydronephrotic neonatal kidney, obstructive nephropathy, renal ischemia-reperfusion, myofibrillar myopathis, pancreas disorders, pancreatitis, pancreatic acinar cell injuries, systemic lupus erythematous (SLE) and urinary tract obstruction.

The subject invention further provides a method of treating cancer comprising administering a pharmaceutically effective amount of a peptide of the invention or a homolog or a derivative thereof and a pharmaceutically acceptable carrier to a subject in need thereof. The subject invention further provides a method of treating cancer comprising administering a pharmaceutically effective amount of an antibody of the invention and a pharmaceutically acceptable carrier to a subject in need thereof. The subject invention also provides a method of treating cancer comprising administering a pharmaceutically effective amount of a fusion protein of the invention and a pharmaceutically acceptable carrier to a subject in need thereof. In one embodiment, the cancer is selected from the group consisting of breast cancer, prostate cancer, lung cancer, colorectal cancer, melanoma, renal cancer, bladder cancer and pancreatic cancer. In a specific embodiment, the cancer is breast cancer. In another specific embodiment, the cancer is lung cancer. In yet another specific embodiment, the cancer is prostate cancer. In yet another specific embodiment, the cancer is colorectal cancer. In yet another specific embodiment, the cancer is melanoma.

The term "treating cancer" in the context of the present invention should be understood to encompass a decrease in tumor size; decrease in rate of tumor growth; stasis of tumor size; decrease in the number of metastasis; decrease in the number of additional metastasis; decrease in invasiveness of the cancer; decrease in the rate of progression of the tumor from one stage to the next, inhibition of tumor growth in a tissue of a mammal having a malignant cancer, control of establishment of metastases, inhibition of tumor metastases formation, regression of established tumors as well as decrease in the angiogenesis induced by the cancer. The term "treating cancer" can also refer to prophylaxis such as prevention as cancer reoccurs after previous treatment (including surgical removal) and prevention of cancer in an individual prone (genetically, due to life style, chronic inflammation and so forth) to develop cancer.

As used herein, a subject can be a male or a female subject; a subject can be a human subject or any other mammal.

The subject invention further provides a method of inhibiting the epithelial-to-mesenchymal transition of carcinoma cells comprising administering a pharmaceutically effective amount of a peptide of the invention or a homolog or a derivative thereof, and a pharmaceutically acceptable carrier to a subject in need thereof. The subject invention further provides a method of inhibiting the epithelial-to-mesenchymal transition of carcinoma cells comprising administering a pharmaceutically effective amount of an antibody of the invention and a pharmaceutically acceptable carrier to a subject in need thereof. The subject invention also provides a method of inhibiting the epithelial-to-mesenchymal transition of carcinoma cells comprising administering a pharmaceutically effective amount of a fusion protein of the invention and a pharmaceutically acceptable carrier to a subject in need thereof.

The term "inhibition of epithelial-to-mesenchymal transition of carcinoma cells" in the context of the present invention should be understood to encompass a decrease in metastatic potential and/or aggressiveness of the tumor cells.

The subject invention further provides a method of treating a neurodegenerative disease comprising administering a pharmaceutically effective amount of a peptide according to the invention or a homolog or a derivative thereof and a pharmaceutically acceptable carrier to a subject in need thereof. The subject invention further provides a method of treating a neurodegenerative disease comprising administering a pharmaceutically effective amount of an antibody of the invention and a pharmaceutically acceptable carrier to a subject in need thereof. The subject invention also provides a method of treating a neurodegenerative disease comprising administering a pharmaceutically effective amount of a fusion protein of the invention and a pharmaceutically acceptable carrier to a subject in need thereof. In one embodiment, the neurodegenerative disease is selected form the group consisting of Alzheimer's Disease, age-related macular degeneration, Creutzfeldt-Jakob disease, radiotherapy induced dementia, axon injury, acute cortical spreading depression, alpha-synucleinopathies, brain ischemia, Huntington's disease, permanent focal cerebral ischemia, peripheral nerve regeneration, post-status epilepticus model, spinal cord injury, sporadic amyotrophic lateralsclerosis and transmissible spongiform encephalopathy.

The term "treating a neurodegenerative disease" in the context of the present invention should be understood to encompass curing of, a slowing of, or a reversal of the progress of the disease in an individual that has been diagnosed as having, or has one or more indicia of, neurodegenerative disease. Treating a neurodegenerative disease includes reducing, lessening or improving one or more of the symptoms of the disease; as well as slowing of, or stopping, the onset of the disease or of one or more of the symptoms thereof.

The subject invention further provides a method of treating a disease related to inflammation of the gastrointestinal tract comprising administering a pharmaceutically effective amount of a peptide according to the invention or a homolog or a derivative thereof, and a pharmaceutically acceptable carrier to a subject in need thereof. The subject invention further provides a method of treating a disease related to inflammation of the gastrointestinal tract comprising administering a pharmaceutically effective amount of an antibody of the invention and a pharmaceutically acceptable carrier to a subject in need thereof. The subject invention also provides a method of treating a disease related to inflammation of the gastrointestinal tract comprising administering a pharmaceutically effective amount of a fusion protein of the invention and a pharmaceutically acceptable carrier to a subject in need thereof. In one embodiment, the disease related to inflammation of the gastrointestinal tract is selected from the group consisting of Crohn's disease, Ulcerative colitis, Celiac disease, inflammatory bowel disease, enteritis, gastritis, gastroenteritis, colitis, enterocolitis, Cholecystitis, Pancreatitis, Irritable bowel syndrome, Caecitis, and Cirrhosis.

The term "treating a disease related to inflammation of the gastrointestinal tract" in the context of the present invention should be understood to encompass curing of, a slowing of, or a reversal of the progress of, the disease in an individual that has been diagnosed as having, or has one or more indicia of disease related to inflammation of the gastrointestinal tract. Treating a disease related to inflammation of the gastrointestinal tract includes reducing, lessening or improving one or more of the symptoms of the disease; as well as slowing of, or stopping, the onset of the disease or of one or more of the symptoms thereof.

The subject invention further provides a method of treating a pathological disorder characterized by increased oxidative stress, comprising administering a pharmaceutically effective amount of a peptide according to the invention or a homolog or a derivative thereof and a pharmaceutically acceptable carrier to a subject in need thereof.

The subject invention further provides a method of treating a pathological disorder characterized by increased oxidative stress comprising administering a pharmaceutically effective amount of an antibody of the invention and a pharmaceutically acceptable carrier to a subject in need thereof. The subject invention also provides a method of treating a pathological disorder characterized by increased oxidative stress comprising administering a pharmaceutically effective amount of a fusion protein of the invention and a pharmaceutically acceptable carrier to a subject in need thereof. In one embodiment, the pathological disorder characterized by increased oxidative stress is selected form the group consisting of ageing, cardiovascular disease, atherosclerotic aorta, myocardial infraction, myocarditis, vascular injury, chronic leg ulcers, diabetes mellitus, eye disorders, ocular surface disease, pseudoexfoliation syndrome, retinal degeneration, kidney degeneration, cystic kidney disease, hydronephrotic neonatal kidney, obstructive nephropathy, renal ischemia-reperfusion, myofibrillar myopathis, pancreas disorders, pancreatitis, pancreatic acinar cell injuries, systemic lupus erythematous (SLE) and urinary tract obstruction.

The term "treating a pathological disorder characterized by increased oxidative stress" in the context of the present invention should be understood to encompass curing of, a slowing of, or a reversal of the progress of the disease in an individual that has been diagnosed as having, or has one or more indicia of disease related to a pathological disorder characterized by increased oxidative stress. Treating a disease related to a pathological disorder characterized by increased oxidative stress includes reducing, lessening or improving one or more of the symptoms of the disease; as well as slowing of, or stopping, the onset of the disease or of one or more of the symptoms thereof.

A peptide, antibody, fusion protein or pharmaceutical composition of the invention may be administered in conjunction with other compounds, including, but not limited to, estrogens, androgens, progestagens, tamoxifen, antiprogestagens, chemotherapeutic agents such as cytotoxic and cytostatic agents, immunological modifiers such as interferons and interleukins, growth hormones or other cytokines, folic acid, vitamins, minerals, aromatase inhibitors, RNAi, Histone Deacetylase Inhibitors proteasome inhibitors, and/or in combination with surgery and/or radiation therapy and so forth.

Non-limiting examples of chemotherapeutic cytotoxic agents which may be administered in conjunction with CGEN-CL1 (or a homolog or a derivative thereof) are alkylating agents, e.g. cyclophosphamide (CTX) (Bristol-Meyers Squibb), ifosfamide (Bristol-Meyers Squibb), chlorambucil (Glaxo Wellcome), and carmustine (Bristol-Meyers Squibb); anti-metabolites, e.g. cytarabine (Pharmacia & Upjohn), 6-mercaptopurine (Glaxo Wellcome), 6-thioguanine (Glaxo Wellcome), and methotrexate (Immunex); antibiotics, e.g. doxorubicin (Pharmacia & Upjohn), daunorubicin (NeXstar), and mitoxantrone (Immunex); agents such as vincristine (Lilly), vinblastine (Lilly), and paclitaxel (Bristol-Meyers Squibb); aromatase inhibitors such as Anastrozole (trade name: Arimidex®, AstraZeneca group); RNAi such as ISIS 3521 (ISIS Pharmaceuticals Inc); Histone Deacetylase Inhibitors such as vorinostat (trade name: ZOLINZA, Merck); and proteasome inhibitors such as bortezomib (trade name: velcade, Millennium Pharmaceuticals). In one embodiment of the present invention, the cytotoxic agent is paclitaxel.

Without being bound by theory, it is possible that a peptide of the invention interferes with internal segment-segment interactions of sCLU thereby preventing it from reaching its active state.

Without being bound by theory, the mechanism of action of a peptide of the invention may concern binding to the parent protein (Clusterin, SEQ ID NO:14) to the segment corresponding to a partner helix of the peptide of the invention.

The subject invention further provides a (poly)nucleotide sequence encoding a peptide of the invention or a homolog thereof.

As used herein "a (poly)nucleotide sequence encoding a peptide of the invention or a homolog thereof" should be understood to encompass any nucleotide sequence encoding a peptide of the invention or a homolog thereof. As known to a person skilled in the art, due to the known degeneracy of the genetic code (codon variability), amino acids can be coded for by more than one codon. Indeed, some amino acids have as many as six alternative codons (e.g. leucine) while some others have a single, required codon (e.g. methionine).

In one embodiment, a polynucleotide sequence of the invention is that encoding SEQ ID NO:1. In one embodiment, the nucleotide sequence is that depicted in SEQ ID NO:2.

In another embodiment, a polynucleotide sequence of the invention is that encoding SEQ ID NO:3. In one embodiment, the nucleotide sequence is that depicted in SEQ ID NO:4.

The term "antibody" as used herein should be understood to encompass a polypeptide ligand substantially encoded by an immunoglobulin gene or immunoglobulin genes, or fragments thereof, which specifically bind and recognize an epitope (e.g., an antigen).

The antibody can be provided as, e.g., an intact immunoglobulin or as a fragment, e.g., a fragment produced by digestion with various peptidases. This includes, e.g. Fab' and F(ab')$_2$ Fv fragments (defined as a genetically engineered fragment containing the variable region of the light chain and the variable region of the heavy chain expressed as two chains) and single chain antibodies ("SCAs"), genetically engineered molecules containing the variable region of the light chain and the variable region of the heavy chain, linked by a suitable polypeptide linker as a genetically fused single chain molecule.

The term "antibody," as used herein, also includes antibody fragments produced e.g. by modification of whole antibodies or synthesized de novo using recombinant DNA methodologies.

The term "antibody" includes, but is not limited to, polyclonal antibodies, monoclonal antibodies, chimeric antibodies, humanized antibodies, or single chain antibodies. In one embodiment, an antibody of the invention is a monoclonal antibody.

"Fc" portion of an antibody refers to that portion of an immunoglobulin heavy chain that comprises one or more heavy chain constant region domains, CH1, CH2 and CH3, but does not include the heavy chain variable region.

An antibody of the invention may be conjugated or coupled to e.g. a detectable label, a radioactive label, an enzyme, a fluorescent label, a luminescent label, a bioluminescent label, a therapeutic agent and so forth.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments may be prepared by proteolytic hydrolysis of the antibody or by expression in e.g. *E. coli* or mammalian cells (e.g. Chinese hamster ovary cell culture or other protein expression systems) of DNA encoding the fragment. Antibody fragments can be obtained by pepsin or papain digestion of whole antibodies by conventional methods.

The antibody may e.g. correspond to a single complementary-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, *Larrick and Fry Methods*, 2: 106-10 (1991).

Humanized forms of non-human (e.g., murine) antibodies may be chimeric molecules of immunoglobulins, or immunoglobulin chains or fragments thereof (such as Fv, Fab, Fab', F(ab') or other antigen-binding subsequences of antibodies) which contain a short sequence, typically of about 20-50 amino acids, derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework (FR) sequences. In general, the humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally will also comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be performed by, for example, substituting rodent CDRs or other CDR sequences for the corresponding sequences of a human antibody. Accordingly, such humanized antibodies are chimeric antibodies (see e.g. U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in e.g. rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be prepared by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., *Bio/Technology* 10: 779-783 (1992); Lonberg et al., *Nature* 368: 856-859 (1994); Morrison, *Nature* 368 812-13 (1994); Fishwild et al., *Nature Biotechnology* 14, 845-51 (1996); Neuberger, *Nature Biotechnology* 14: 826 (1996); and Lonberg and Huszar, *Intern. Rev. Immunol.* 13, 65-93 (1995).

An antibody of the invention binds specifically (or selectively) to a peptide of the invention. The term "specifically (or selectively) binds" to a peptide or the term "specifically (or selectively) immunoreactive with," when referring to a protein or peptide, refers to a binding reaction that is determinative of the presence of the peptide in a heterogeneous population of peptide and other biologics. Thus, under designated immunoassay conditions, the specified antibodies bind to a particular peptide at least twice the background and do not substantially bind in a significant amount to other proteins or peptides present in the sample. Specific binding to an antibody under such conditions may require an antibody that is selected for its specificity to a particular peptide. A variety of immunoassay formats may be used to select antibodies specifically immunoreactive with a particular peptide. For example, solid-phase ELISA immunoassays are routinely used to select antibodies specifically immunoreactive with a protein or a peptide (see, e.g., Harlow & Lane, Antibodies, A Laboratory Manual (1988)). Typically a specific or selective reaction will be at least twice the background signal or noise and more typically more than 10 to 100 times background.

The terms "conjugate" and "fusion protein" and any lingual derivatives thereof are interchangeably used herein.

The subject invention further provides a peptide of the present invention conjugated or fused to another peptide or to a polypeptide. Such conjugates/fusion proteins may be prepared by any methodology known in the art such as, but not limited to the preparation of conjugates/fusion proteins using chemical synthesis or using recombinant technology.

Examples of peptides or polypeptides which may be conjugated/fused to a peptide of the invention are multiple antigenic peptides (MAP), Fc chains of immunoglobulins and signal sequences.

In one embodiment, a peptide or a polypeptide which may be conjugated to a peptide of the invention is an immunoglobulin sequence (e.g., an IgG sequence). Non-limiting examples of immunoreactive ligands (which may e.g. serve as a targeting moiety) are an antigen-recognizing immunoglobulin (also referred to herein as "antibody") and an antigen-recognizing fragment thereof, e.g., immunoglobulins that can recognize a (tumor-associated) antigen.

As used herein, "immunoglobulin" should be understood to refer to any recognized class or subclass of immunoglobulins such as IgG, IgA, IgM, IgD, or IgE. In one embodiment, the immunoglobulin is within the IgG class of immunoglobulins. The immunoglobulin may be derived from any species, such as, but not limited to human, murine, or rabbit origin. In addition, the immunoglobulin may be polyclonal or monoclonal. In one embodiment, the immunoglobulin is monoclonal.

A conjugate/fusion protein may be prepared from a peptide according to the present invention by fusion with e.g. a portion of an immunoglobulin comprising a constant region of an immunoglobulin. In one embodiment, the portion of the immunoglobulin comprises a heavy chain constant region. In another embodiment, the heavy chain constant region comprises a human heavy chain constant region. In yet another embodiment, the heavy chain constant region is an IgG heavy chain constant region.

In yet another embodiment, the heavy chain constant region is an Fc chain. In yet another embodiment, the Fc chain is an IgG Fc fragment that comprises CH2 and CH3 domains. In yet another embodiment, the IgG Fc fragment is of the IgG1 subtype. The Fc chain may be a known or "wild type" Fc chain, or may be mutated. Non-limiting, illustrative, exemplary types of mutations are described in US Patent Application No. 20060034852, hereby incorporated by reference as if fully set forth herein.

The term "Fc chain" as used herein should be understood to encompass any type of Fc fragment. Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific modifications may result e.g. in glycosylation and/or other desired modifications to the Fc chain. It is envisaged that modifications may be made to e.g. block a function of Fc which is considered to be undesirable, such as an undesirable immune system effect.

Thus, conjugates of the invention (which comprise a peptide of the invention) may comprise an antigen-recognizing immunoglobulin fragment and/or Fc chain. Such immunoglobulin fragments may comprise, for example, the Fab', F(ab')$_2$, Fv or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, *J. Immunology*, 131,2895, 1983; Lamoyi et al., *J. Immunological Methods*, 56,235, 1983.

The following abbreviations should be understood as follows:
Amino Acid Abbreviation IUPAC Symbol:
A=Ala=Alanine
C=Cys=Cysteine
D=Asp=Aspartic Acid
E=Glu=Glutamic Acid
F=Phe=PhenylAlanine
G=Gly=Glycine
H=His=Histidine
I=Ile=Isoleucine
L=Lys=Lysine
M=Met=Methionine N=Asn=Asparagine
P=Pro=Proline
Q=Gln=Glutamine
R=Arg=Arginine
S=Ser=Serine
T=Thr=Threonine
V=Val=Valine
W=Trp=Tryptophan
Y=Tyr=Tyrosine The following abbreviations shall be employed for nucleotide bases: A for adenine; G for guanine; T for thymine; U for uracil; and C for cytosine.

The invention is further described in the following examples, which are not in any way intended to limit the scope of the inventions as claimed.

EXAMPLES

Example 1

Synthesis of a Peptide of the Invention

The peptide FYFWMNGDRIDSLLENDRQQT (CGEN-CL1) [SEQ ID NO: 1] was synthesized by solid-phase peptide synthesis using Fmoc-chemistry at Pepscan Systems (http://www.pepscan.nl). The CGEN-CL1 peptide was amidated at its C-terminus, and acetylated at its N-terminus. CGEN-CL1 has a molecular weight of 2690.1.

The partner helix peptide RLTRKYNELLKSYQWK-MLNTSS [SEQ ID NO: 5] was synthesized by solid-phase peptide synthesis using Fmoc-chemistry at Pepscan Systems (http://www.pepscan.nl). The partner helix peptide [SEQ ID NO: 5] was amidated at its C-terminus, and acetylated at its N-terminus, and has a molecular weight of 2760.2.

Example 2

Analysis of Activity of CGEN-CL1 Peptide in Various Cancer Cell Lines

CGEN-CL1 as synthesized in Example 1 was analyzed for its ability to induce growth arrest in various cancer cell lines, such as: breast cancer cell line MCF-7 (Adenocarcinoma, Breast, HTB-22, ATCC), PC3 (Adenocarcinoma, Prostate, CRL-1435, ATCC), A549 (carcinoma, Lung, CCL-185, ATCC), HT-29 (Colorectal Adenocarcinoma, Colon, HTB-38, ATCC) and SK-mel 5 (Melanoma, Skin, HTB70, ATCC).

MCF7 cells were seeded at 10,000 cells per well in 150 µl of media (DMEM medium+5% FBS) in a 96 well plate.

PC3 cells were seeded at 8000 cells per well in 150 µl of media (DMEM medium+5% FBS) in a 96 well plate.

A549 cells were seeded at 6000 cells per well in 150 µl of media (DMEM medium+5% FBS) in a 96 well plate.

HT29 cells were seeded at 10,000 cells per well in 150 µl of media (DMEM medium+5% FBS) in a 96 well plate.

SK-MEL 5 cells were seeded at 10,000 cells per well in 150 µl of media (DMEM medium+5% FBS) in a 96 well plate.

CGEN-CL1 (1 mg dissolved in 2500 of Sodium bi-carbonate to a stock concentration of 4 mg/ml) was added to the wells in 500 of medium (final volume of 2000) as detailed in Table 2. The relative growth was normalized to controls where CGEN-CL1 was not added to wells.

TABLE 2

| Plate | Day 1   | Day 2                   | Day 3 | Day 4 |
|-------|---------|-------------------------|-------|-------|
| 1     | seeding | 50 µl CGEN-CL1 in medium | —     | MTT   |

MTT Assay:

20 µl of MTT (3-(4,5-Dimethyl-2-thiazolyl)-2,5-diphenyl-2H-tetrazolium bromide) solution (Sigma Cat#M5655, lot#085k5322, 1 gr was dissolved in 200 ml H2O and filtered, giving a final concentration of 5 mg/ml) was added to each well and incubated for 4 hours at 37° C. after which the medium was vacuumed and 100 µl of DMSO was added to each well. Absorbance was measured in an ELISA reader at 492 nm.

FIG. 1A represents the relative growth of MCF-7 cells, treated with various doses of CGEN-CL1, normalized to untreated control (when the CGEN-CL1 concentration equals 0 the cells are untreated control).

As demonstrated in FIG. 1A, as little as 50 nM of CGEN-CL-1 had a growth inhibiting effect when applied to MCF-7 breast cancer cells. The $EC_{50}$ of CGEN-CL1 was 56 nM.

As shown in FIG. 1A maximal growth inhibition of the breast cancer cells was achieved with approximately 900 nM of CGEN-CL1.

Figure 1B:
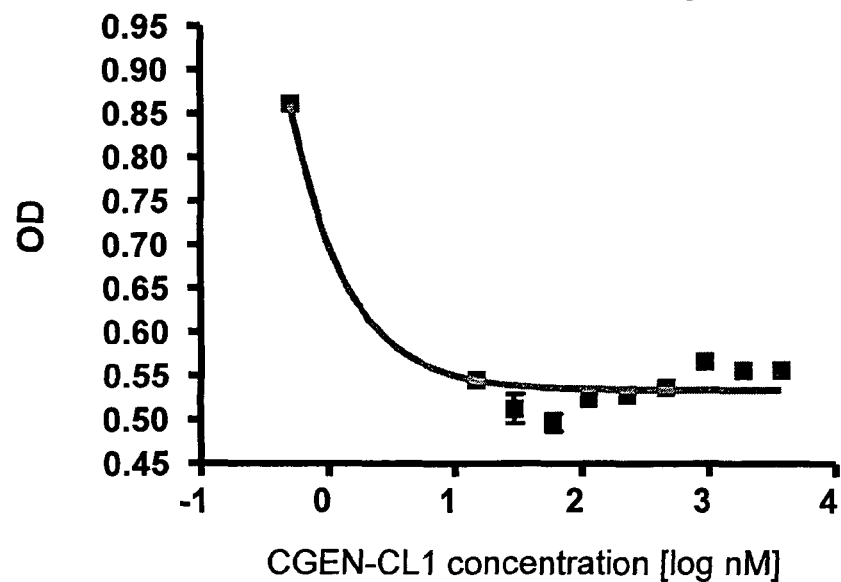

FIG. 1B reveals the growth inhibition of PC3 cells, induced by various doses of CGEN-CL1. As shown in FIG. 1B, as little as 15 nM of CGEN-CL1 evoked the maximal effect of about 40% growth inhibition of PC3 cells.

Figure 1C:
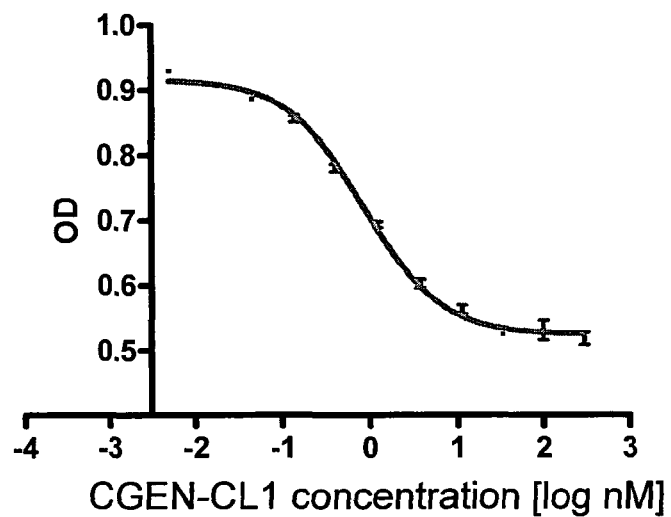
Figure 1D:
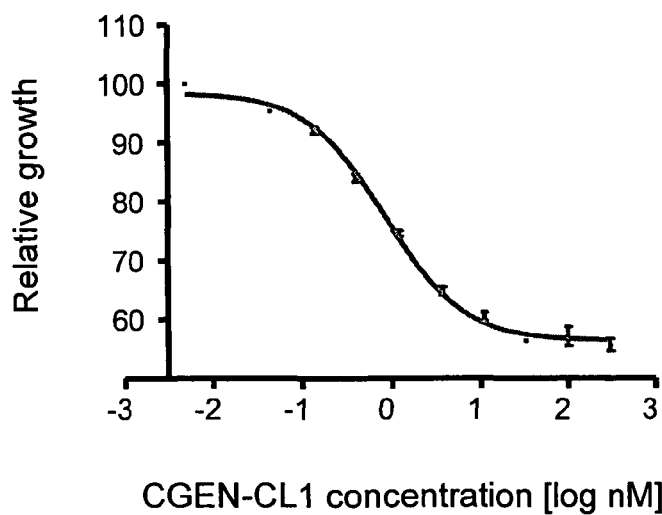

FIGS. 1C and 1D demonstrate that CGEN-CL1 [SEQ ID NO:1] evoked growth inhibition of A549 human non-small cell lung cancer cells (absolute reads or normalized to non-treated respectively) as revealed by cellular viability. For this cell line the effect of CGEN-CL1 was the most prominent with an EC50 of 0.95 nM.

Figure 1E:
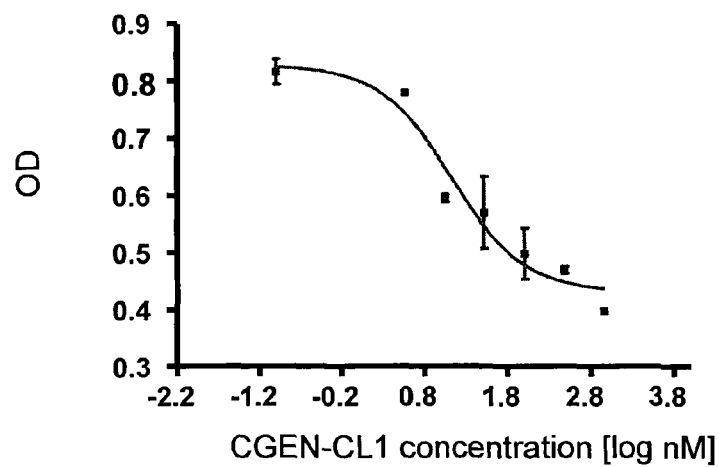
Figure 1F:
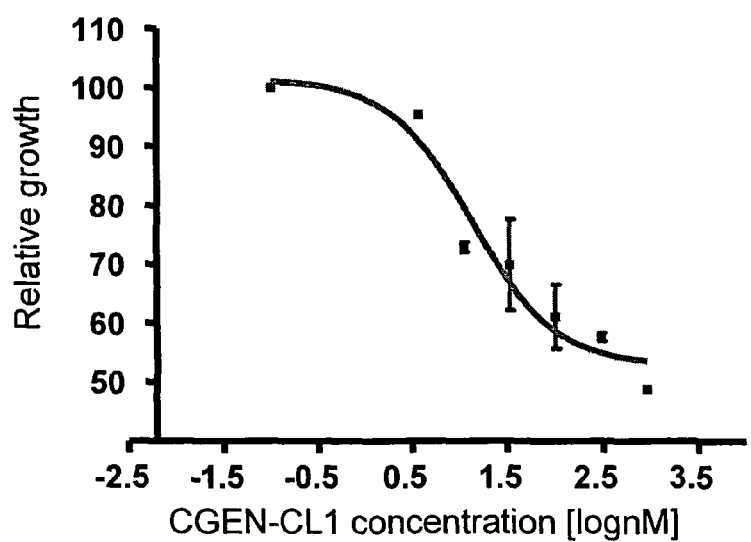

FIGS. 1E and 1F demonstrate that CGEN-CL1 [SEQ ID NO:1] evoked growth inhibition of HT29 colorectal adenocarcinoma cells (absolute reads or normalized to non-treated respectively) as revealed by cellular viability.

Figure 1G:
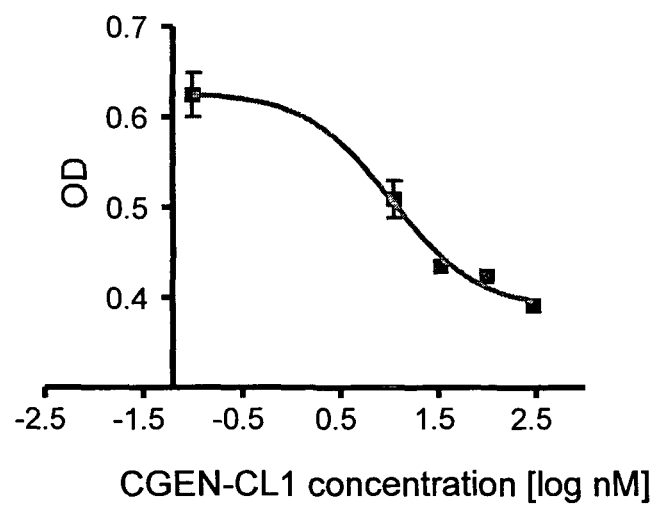
Figure 1H:
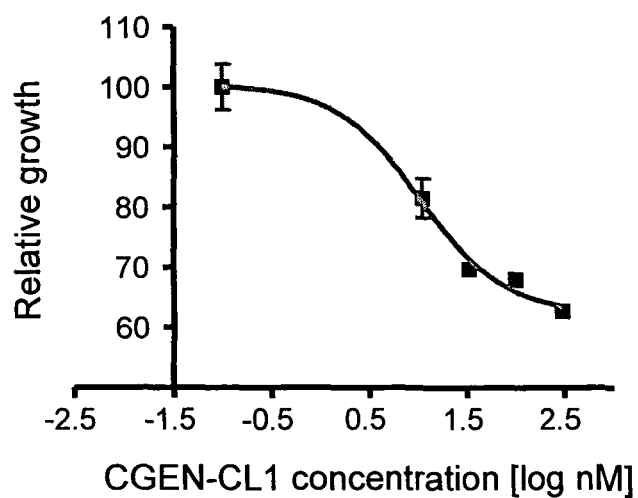

FIGS. 1G and 1H demonstrate that CGEN-CL1 [SEQ ID NO:1] evoked growth inhibition of SK-MEL melanoma cells (absolute reads or normalized to non-treated respectively) as revealed by cellular viability.

Example 3

Effect of CGEN-CL-1 on Induction of Apoptosis in PC3 Cells

In order to analyze the effect of CGEN-CL-1 [SEQ ID NO:1] on induction of apoptosis in PC3 cells, PC3 cells were treated with 300 nM of CGEN-CL-1 [SEQ ID NO:1], incubated for 48 hours and treated with an additional dose of 300 nM of CGEN-CL-1 [SEQ ID NO:1]. Apoptosis was analyzed either by cell cycle analysis or by PARP cleavage estimation. The amount of cleaved PARP is proportional to the amount of cells undergoing apoptosis (see for example Boulares A. H., et al., 1999, *JBC* 274:22932-22940).

Cell Cycle Analysis was carried out by Propidium Iodide (PI) Staining. The cells were trypsinized and suspended in DMEM medium+10% FCS. Following centrifugation (1000 rpm, 5 min) the cell pellet was suspended in PBS (1 ml). Fixation with EtOH was performed as follows: cell suspension was transferred into 2.5 ml absolute EtOH (final concentration approx. 70%) by pipetting or by vortexing the suspension at half speed while adding the EtOH) to prevent clustering of cells during the fixation. EtOH fixed cells were incubated on ice for 15 min (or overnight at −20° C.).

Propidium Iodide (PI) staining of the cells was carried out as follows: the cells were pelleted at 1500 rpm for 5 min and then suspended in 500 μl PI-solution (in PBS: 50 μg/ml PI from 50× stock solution (2.5 mg/ml); 0.1 mg/ml RNase A; 0.05% Triton X-100), following incubation for 40 min at 37° C. Then 3 ml of PBS were added, and the cells were pelleted at 1500 rpm, 5 min. The cell pellet was suspended in 500 μl PBS for flow analysis. The flow analysis was carried out using the following approximate settings (on FACSort): FL1: 570 V log; FL2: 470 V linear.

Figure 2A:
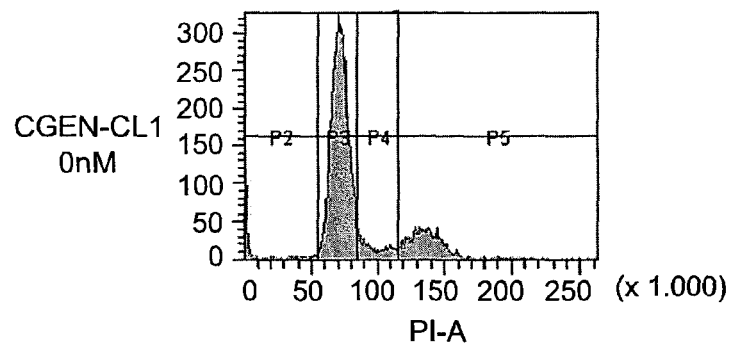
FIGS. 2A-2D demonstrate the results of Cell Cycle Analysis as revealed by FACS analysis of Propidium Iodide (PI-A) Stained PC3 cells treated with CGEN-CL1.
Figure 2B:
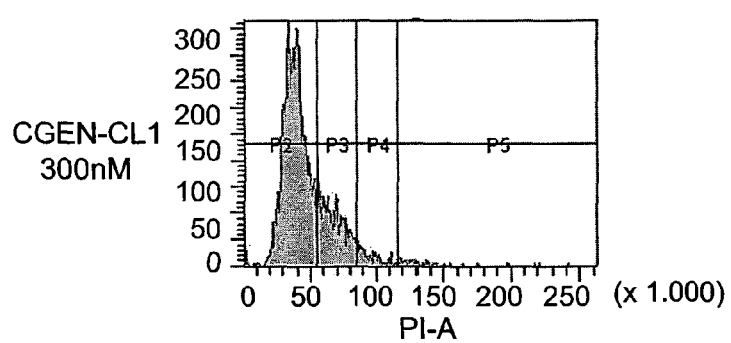
Figure 2C:
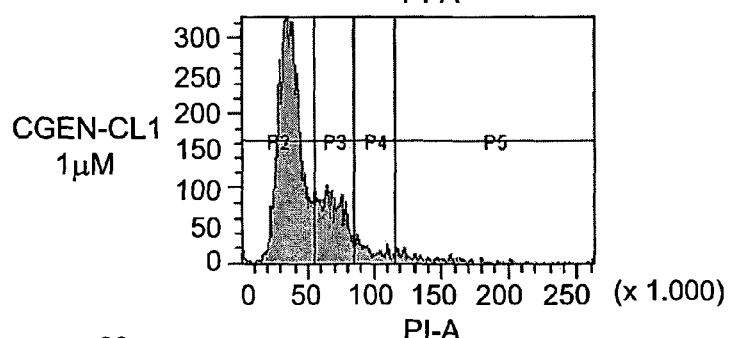
Figure 2D:
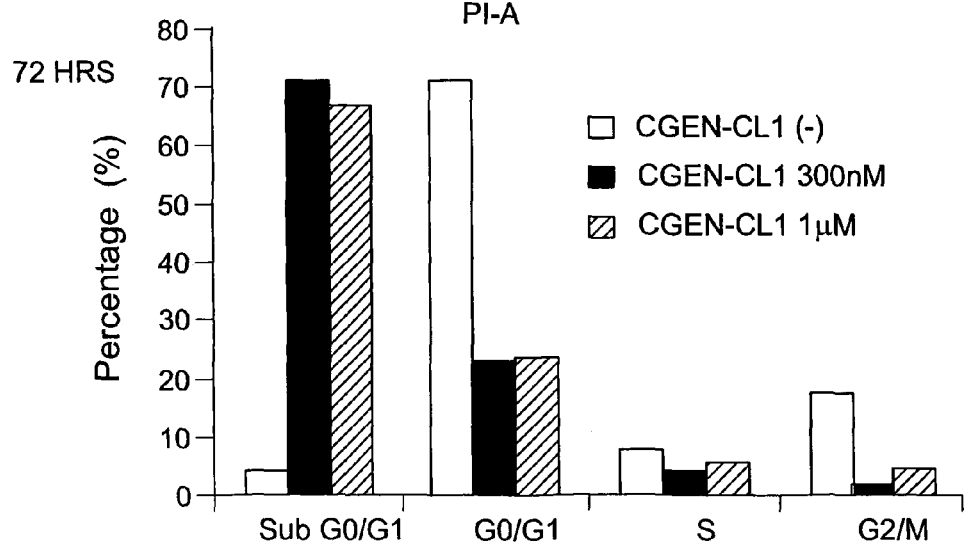

The results are shown in FIGS. 2A-2D and 3. FIGS. 2A-2D demonstrate that treatment of PC3 cells with CGEN-CL1 (SEQ ID NO:1) increased the percentage of apoptotic cells and increased the percentage of cells in cell cycle phases G0/G1 and G2/M. FIGS. 2A-2D present the results of Cell Cycle Analysis by Propidium Iodide (PI) Staining in CGEN-CL1-treated PC3 cells. FIG. 2A presents untreated PC3 cells; FIG. 2B presents cells treated with 300 nM of CGEN-CL-1 [SEQ ID NO:1]; and FIG. 2C presents cells treated with 1 μM of CGEN-CL-1 [SEQ ID NO:1]. FIG. 2D presents graphically the percentage of cells in the different stages of cell cycle.

Figure 3:
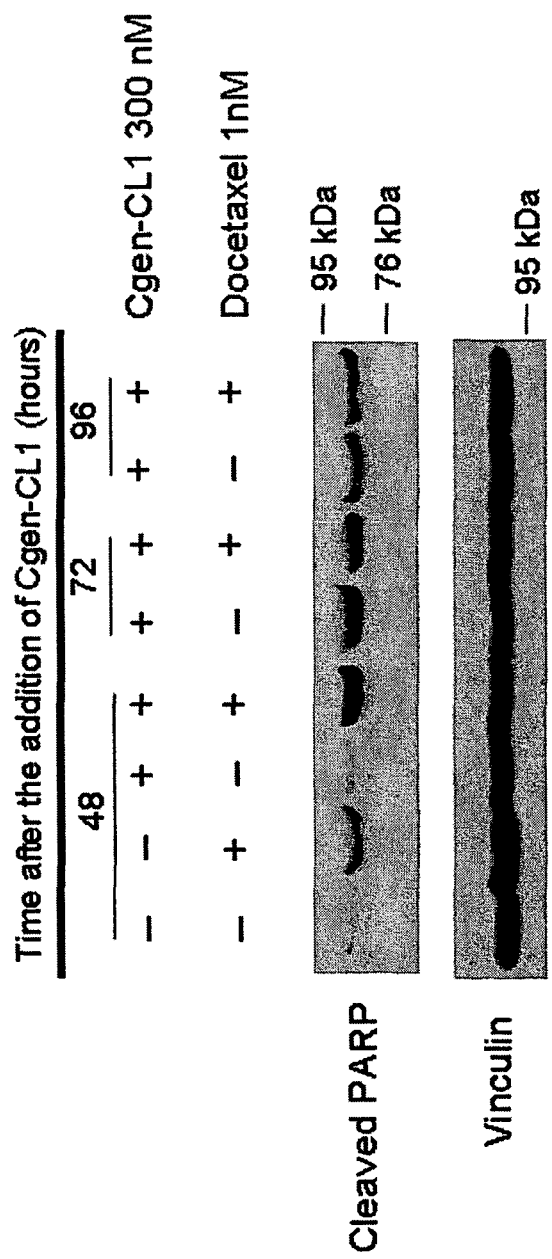
FIG. 3 demonstrates results of detection of cleaved PARP in PC3 cells treated with different doses of CGEN-CL1 [SEQ ID NO:1] alone or in combination with Docetaxel (Paclitaxel). A house keeping gene Vinculin, which is not effected by the treatment, was used as a control to confirm same amount of cells loaded in each well. The amount of cleaved PARP is proportional to the amount of cells undergoing apoptosis.

FIG. 3 presents results of detection of cleaved PARP in PC3 cells treated with CGEN-CL1 combined with or without Paclitaxel. PC3 cells were treated with CGEN-CL1 (SEQ ID NO:1), alone or in combination with Paclitaxel, for 48, 72 and 96 hours. Cleaved PARP was detected in cell lysates by Western blot analysis. FIG. 3 demonstrates that the treatment with CGEN-CL1 (SEQ ID NO:1) for 48 hours caused an enhancement in the amount of cleaved PARP and dramatically enhanced the amount of cleaved PARP in cells treated with Paclitaxel. Treatment of PC3 cells for 72 hours with CGEN-CL1 [SEQ ID NO:1] alone, one administration in time zero and another after 48 hours, gave rise to a significant increase in cleaved PARP. Elevation of the amount of cleaved PARP indicates an increase in apoptotic cells.

This example thus demonstrates that treatment of PC3 prostate cancer cells with CGEN-CL1 gave rise to a significant increase in cells undergoing apoptosis. These observations support that CGEN-CL1 functions as a specific and potent anti-cancer agent, potentially acting as an inhibitor of Clusterin, which is known to be involved in mechanisms enabling escape from apoptosis.

Example 4

Administration of CGEN-CL1 with Paclitaxel on Various Cancer Cell Lines

A549, PC3 and MCF7 cells were seeded at 6000, 8000 and 10,000 cells per well respectively in 150 μl of media (DMEM medium+5% FBS) in 96 well plates.

Paclitaxel (Sigma T7402, Lot. 036k1217, Mw 853.9, 5 mg dissolved in 585 μl DMSO to a stock concentration of 10 mM, stored at −20° C.) and/or CGEN-CL1 (1 mg dissolved in 250 μl of sodium bi-carbonate to a stock concentration of 4 mg/ml) were added to the wells in 25 μl of medium (final volume of 200 μl) as detailed in Table 3. The relative growth was normalized to controls where neither paclitaxel nor CGEN-CL1 was added to wells.

An MTT assay was performed as described above in Example 2.

TABLE 3

| Plate | Day 1 | Day 2 | Day 3 | Day 4 |
|---|---|---|---|---|
|  | seeding | 25 μl paclitaxel and/or 25 μl CGEN-CL1 | — | MTT |

Table 4 demonstrates that at 30 nM Paclitaxel, the addition of as little as 7.1 nM of CGEN-CL1 resulted in further inhibition of cell proliferation. Furthermore, using a sub-minimal concentration of Paclitaxel (2.25 nM) in combination with 22.3 nM of CGEN-CL1 resulted in a similar extent of cell proliferation inhibition as achieved by Paclitaxel alone at a concentration that results in a maximal effect. Therefore using CGEN-CL1 in combination with Paclitaxel enables the use of lower concentrations of Paclitaxel, in order to achieve a similar effect, thereby enabling the reduction of side effects caused by chemotherapy.

TABLE 4 effect of CGEN-CL1 and paclitaxel on growth of MCF-7 breast cancer cell lines as revealed by MTT assay.

| CGEN-CL1(nM) | Paclitaxel(nM) | Relative Growth |
|---|---|---|
| 0.0 | 0.00 | 1.00 |
| 0.0 | 2.25 | 0.88 |
| 0.0 | 30.00 | 0.49 |
| 7.1 | 0.00 | 0.68 |
| 7.1 | 2.25 | 0.62 |
| 7.1 | 30.00 | 0.31 |
| 22.3 | 0.00 | 0.61 |
| 22.3 | 2.25 | 0.53 |
| 22.3 | 30.00 | 0.28 |
| 63.2 | 0.00 | 0.48 |
| 63.2 | 2.25 | 0.46 |
| 63.2 | 30.00 | 0.24 |
| 185.9 | 0.00 | 0.49 |
| 185.9 | 2.25 | 0.45 |
| 185.9 | 30.00 | 0.25 |
| 557.6 | 0.00 | 0.46 |
| 557.6 | 2.25 | 0.42 |
| 557.6 | 30.00 | 0.23 |

Table 4 also demonstrates that CGEN-CL1 and paclitaxel have a synergistic effect on growth inhibition of the cells when given in combination. Combination indices (CI) for different drug effects were calculated to be between 0.2 and 0.6. It is noteworthy that CI lower than 1 indicates synergy between the two compounds used in combination (Zhao L, Wientjes M G, Au J L. *Evaluation of combination chemotherapy: integration of nonlinear regression, curve shift, isobologram, and combination index analyses. Clin Cancer Res* 2004; 10(23):7994-8004).

Figure 4A:
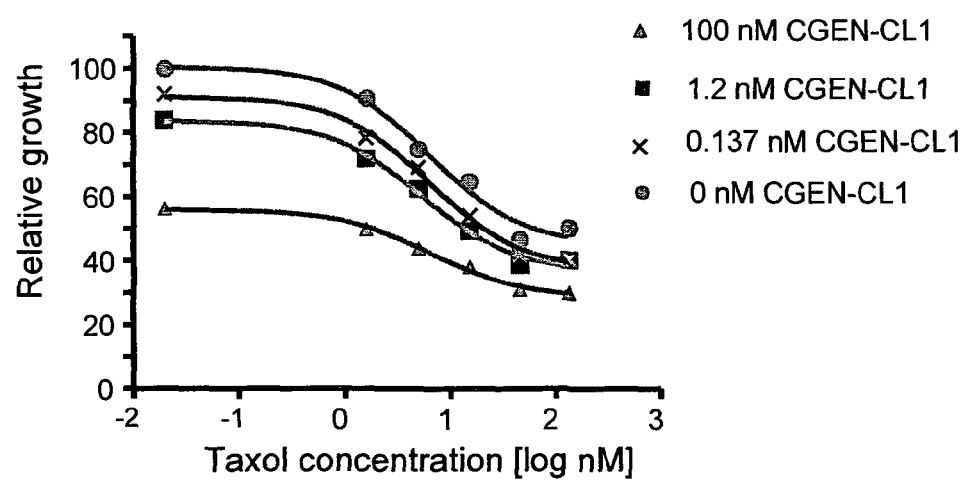
FIG. 4A: effect of paclitaxel (taxol) and CGEN-CL1 on the growth and proliferation of lung carcinoma cell line A549.

FIG. 4A shows that administration of CGEN-CL1 [SEQ ID NO:1] in combination with Paclitaxel to A549 cells increases the sensitivity of the cells to this chemotherapeutic agent: (i) as little as 1 nM of CGEN-CL1 [SEQ ID NO:1] sensitizes A549 cells to sub-minimal concentrations of paclitaxel; (ii) maximal effect of CGEN-CL1 [SEQ ID NO:1] in combination with paclitaxel (73% inhibition) is higher than the maximal effect of CGEN-CL1 alone (48%) and paclitaxel alone (50%).

Thus, (1) combination of CGEN-CL1 [SEQ ID NO:1] with chemotherapy resulted in similar levels of anti-cancer activity with lower doses of chemotherapy compared to higher doses of chemotherapy alone, thus reducing side effects; and (2) treatment with a combination of paclitaxel and CGEN-CL1 [SEQ ID NO:1] achieved a better anti-cancer effect compared to monotherapy.

Figure 4B:
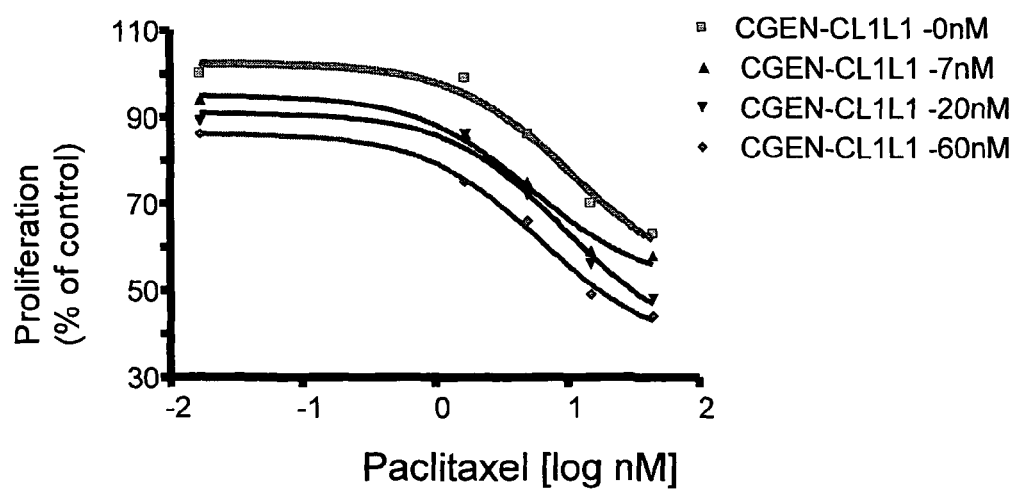
FIG. 4B: effect of paclitaxel and CGEN-CL1 on the growth and proliferation of prostate adenocarcinoma cell line PC3.

FIG. 4B shows the synergistic effect between CGEN-CL1 and paclitaxel when CGEN-CL1 was added at different concentrations to PC3 cells treated with different doses of paclitaxel. As little as 7 nM of CGEN-CL1 sensitized PC3 cells to paclitaxel at sub-minimal doses. 60 nM of CGEN-CL1 when combined with 5 nM of paclitaxel achieved the same growth inhibition rates as the growth inhibition achieved by 45 nM of paclitaxel alone, 60 nM of CGEN-CL1 when combined with 45 nM of paclitaxel achieved 1.5 fold more active growth inhibition than 45 nM of paclitaxel alone.

Figure 5:
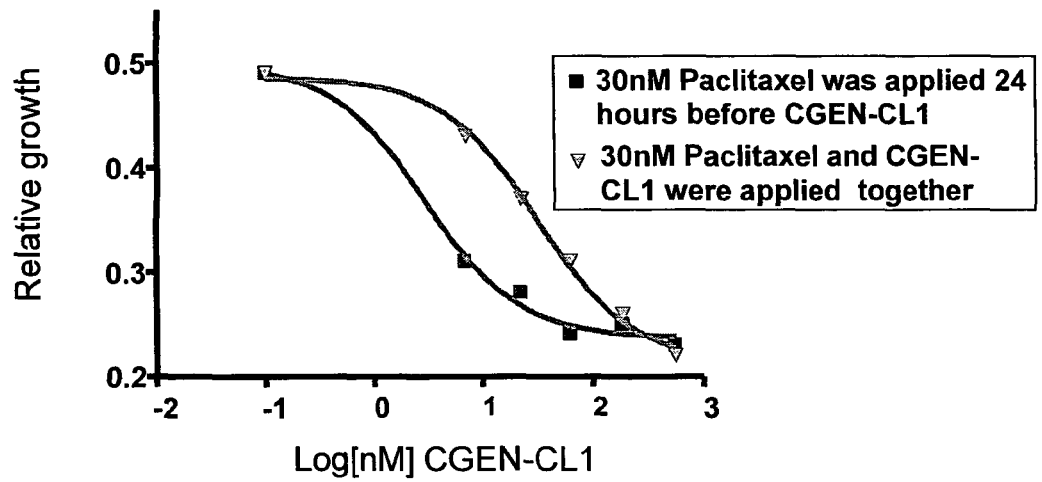
FIG. 5: effect of CGEN-CL1 on cell growth when added to the MCF-7 cell culture 24 hours after the cells were exposed to 30 nM paclitaxel and when added concomitantly with 30 nM paclitaxel to the MCF-7 breast cancer cell culture as revealed by MTT assay.

FIG. 5 shows the effect of CGEN-CL1 on cell growth when added to the MCF-7 cell culture 24 hours after the cells were exposed to 30 nM paclitaxel and when added concomitantly with 30 nM paclitaxel to the MCF-7 breast cancer cell culture as revealed by MTT assay. FIG. 5 demonstrates that treatment with CGEN-CL1 after treatment with Paclitaxel resulted in a need for lower concentrations of CGEN-CL1 to achieve the same effect as when CGEN-CL-1 and paclitaxel were administered simultaneously.

As it is known that treatment with Paclitaxel increases sCLU expression, without being bound by theory, these results point to a possible mechanism wherein CGEN-CL1 acts by blocking sCLU activity.

Example 5

Evaluation of the In Vivo Activity of CGEN-CL1

In order to test the in-vivo activity of CGEN-CL1, Balb/c Nu/Nu female mice (10 in each group) were inoculated with 5×10$^6$ A549 human non-small cell lung cancer cells. Treatment was initiated when tumors reached 400-500 mm$^3$. One group received 15 mg/kg of paclitaxell (IP once every three days) and CGEN-CL1 [SEQ ID NO:1] (daily injected subcutaneously (sc) at the surrounding of the tumor) whereas the second group received paclitaxel and saline (at the same dose and route of administration). Tumor volume was measured every three days.

Figure 6:
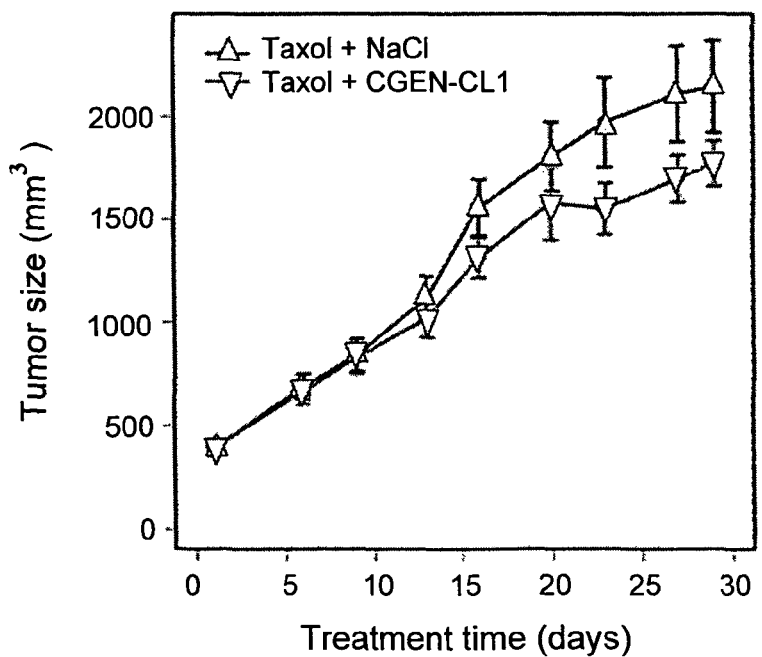
FIG. 6 demonstrates the effect of CGEN-CL1 on paclitaxel (taxol) sensitivity of A549 human non-small cell lung cancer cells derived from tumors in a mouse xenograft model.

As shown in FIG. 6, when applied to tumor bearing BALB/c nu/nu female mice treated with paclitaxel (taxol), CGEN-CL1 [SEQ ID NO:1] injected subcutaneously at the surrounding of the tumor graft resulted in a 25-30% reduction in tumor volume when compared to the control group treated with paclitaxel and vehicle.

Example 6

Design of Conformational Change Blockers of Clusterin

Conformational changes in proteins play a major role in activity regulation. Natural and synthetic molecules that modulate such changes are of considerable biological importance. Such molecules include allosteric effectors that alter the rapidity of enzyme-catalyzed reactions (J. Monod, et al., *J Mol Biol* 12, 88 (1965)), molecules that shift the oligomerization equilibrium of proteins (Z. Hayouka et al., *Proc Natl Acad Sci USA* 104, 8316 (2007)), and molecules that interfere with trans-membrane helix-helix associations (H. Yin et al., *Science* 315, 1817 (2007)). Conformational change modulators of clusterin were designed. The designed peptides were identified using a unique computerized method to interfere with conformational changes involving helix-helix interactions.

The computational approach for sequence-based identification of intra-molecular helix-helix interactions is able to detect interactions that are ordinarily difficult to observe experimentally. The computational approach was based on the analysis of correlated mutations in the sequences of a target protein and its homologs (FIGS. 7A-7D and FIGS. 8A-8D). Such analysis aims at identifying intra-molecular interactions between pairs of amino acid residues (S. S. Choi, et al., *Nat Genet* 37, 1367 (2005)); G. B. Gloor, et al., *Biochemistry* 44, 7156 (2005); U. Gobel, et al., *Proteins* 18, 309 (1994); S. W. Lockless, et al., *Science* 286, 295 (1999); L. C. Martin, M. Wahl, *Bioinformatics* 21, 4116 (2005); F. Pazos, et al., *Comput Appl Biosci* 13, 319 (1997)) (J. Cheng, P. et al., *BMC Bioinformatics* 8, 113 (2007); S. D. Dunn, L. et al., *Bioinformatics* 24, 333 (2008); G. Shackelford, K et al., Karplus, *Proteins* 69 *Suppl* 8, 159 (2007)) facilitated by the introduction of a new category of residue-residue contact prediction into the Critical Assessment of techniques for protein Structure Prediction (CASP) competition (J. M. Izarzugaza, et al., *Proteins* 69 *Suppl* 8, 152 (2007). Nevertheless, despite these algorithmic advances and the growing availability of sequence data, the signal to noise ratio of correlated mutation analysis remains relatively low, and does not currently allow ab initio structure prediction.

Figure 7C:
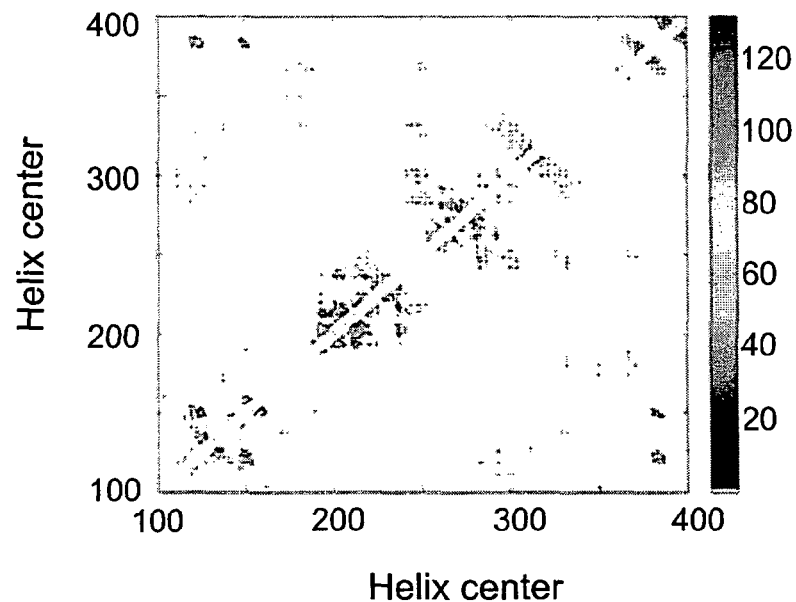
Figure 7D:
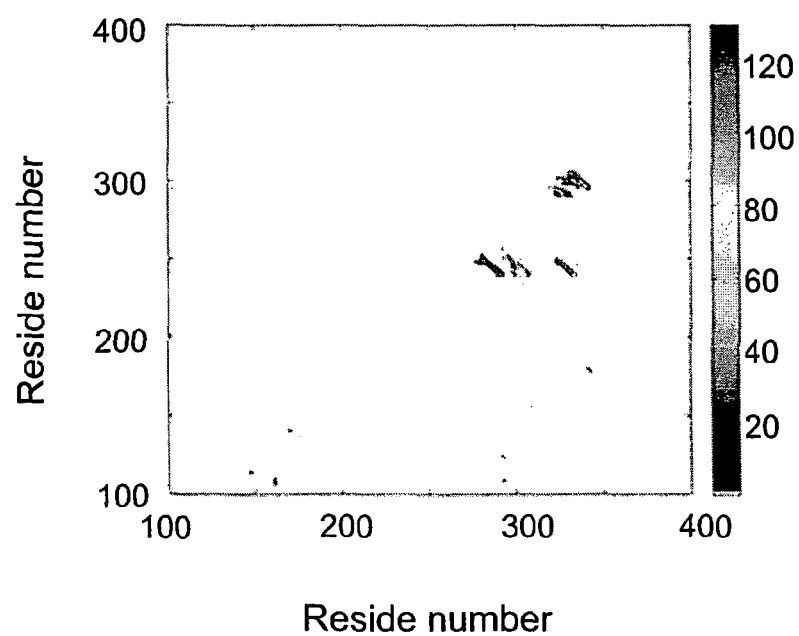

The detection of interacting segments through correlated mutation analysis is thus hindered by the low signal to noise ratio, when applied naively, e.g., averaging over a sliding window approach. The main conceptual new ingredient of the unique in silico approach used herein for identification of peptides capable of acting as conformational change blockers of Clusterin, is the exploitation of the periodic nature of the correlated mutation data for helix-helix interactions, for which the corresponding periodicity should be around 3.6 amino acids (FIGS. 7A-B). Technically, this was achieved using an appropriate application of the Fourier transform. An interaction was detected by a peak in the absolute value of the Fourier transform of the correlated mutations signal around the typical periodicity. Although the transform is one dimensional, it analyses the two dimensional matrix of correlated mutation scores, detecting the periodicity manifested in both interacting segments (FIGS. 7C-7D). In this unique technology, used for computerized detection of peptides capable of acting as conformational change blockers of Clusterin, Fourier transform was introduced to correlated mutations analysis, substantially improving the signal to noise ratio (FIG. 7C vs. FIG. 7D), as well as a "two dimensional" Fourier analysis was employed in protein structure determination.

This newly-developed tool was applied to clusterin, resulting in detection of remarkable peak of the absolute values of the Fourier transform around the expected periodicity.

Using this approach, an interaction between CGEN-CL1 (SEQ ID NO:1) and a helix peptide corresponding to residues 336-357 in clusterin (partner helix) [SEQ ID NO:5] was computationally identified.

FIGS. 7A-7D show the identification using the unique computerized method for prediction of helix-helix interactions. FIG. 7A demonstrates residue-residue contact map of two anti-parallel helices taken from the solved structure of BAG-1 (PDB id: 1HX1 Chain B) calculated using CSU (V. Sobolev, et al., *Bioinformatics* 15, 327 (1999)). FIG. 7B demonstrates a schematic view of two helices interacting through their adjacent faces. This interaction gives rise to the 3.6-residue periodicity that is the basis of the subject new Fourier transform-based approach. Each residue on one helix may interact with 3-4 residues on the other helix spanning a region of 8-9 residues (see red rectangle in FIG. 7A). FIG. 7C demonstrates the residue-residue contact map for clusterin as predicted by SVMcon (J. Cheng, P. et al., *BMC Bioinformatics* 8, 113 (2007)). Typically, in these methods (S. S. Choi, *Nat Genet* 37, 1367 (2005); G. B. Gloor, *Biochemistry* 44, 7156

(2005); U. Gobel, et al., *Proteins* 18, 309 (1994); L. C. Martin, et al., *Bioinformatics* 21, 4116 (2005); F. Pazos, et al., *Comput Appl Biosci* 13, 319 (1997); J. Cheng, et al., *BMC Bioinformatics* 8, 113 (2007); S. D. Dunn, et al., *Bioinformatics* 24, 333 (2008); G. Shackelford, et al., *Proteins* 69 *Suppl* 8, 159 (2007)). the sequences of the protein of interest and its homologs are used for constructing a multiple sequence alignment (MSA). Correlations between columns in the MSA (correlated mutations) point to predicted residue-residue interactions. Until today however, known contact map prediction technologies suffered from low recall and low precision. These drawbacks in helix-helix interactions identification have now been solved by the unique in silico approach used herein for identification of peptides capable of acting as conformational change blockers of Clusterin. FIG. 7D shows a map of scores based on the Fourier transform of the correlated mutation signal of clusterin. In order to detect helix-helix interactions, for each pair of 21-residue long segments two vectors of sums of the predicted residue-residue scores are calculated: one for the rows and one for the columns of the corresponding 21 by 21 matrix. For the detection of parallel helix-helix interactions only the principal (i.e. major) diagonal and its 4 neighboring diagonals from each side are summed. For anti-parallel interactions, the minor diagonal is similarly utilized. The two vectors are then Fourier transformed. A joint score is calculated that is non-zero only if a significant peak representing a periodicity of about 3.6 residues exists in the Fourier Transform of both the 'rows' and the 'column' vectors. FIGS. 7C and 7D demonstrate how the Fourier Transform enhances the signal to noise ratio and enables reliable predictions of parallel helix-helix interaction in clusterin.

Figure 8A:
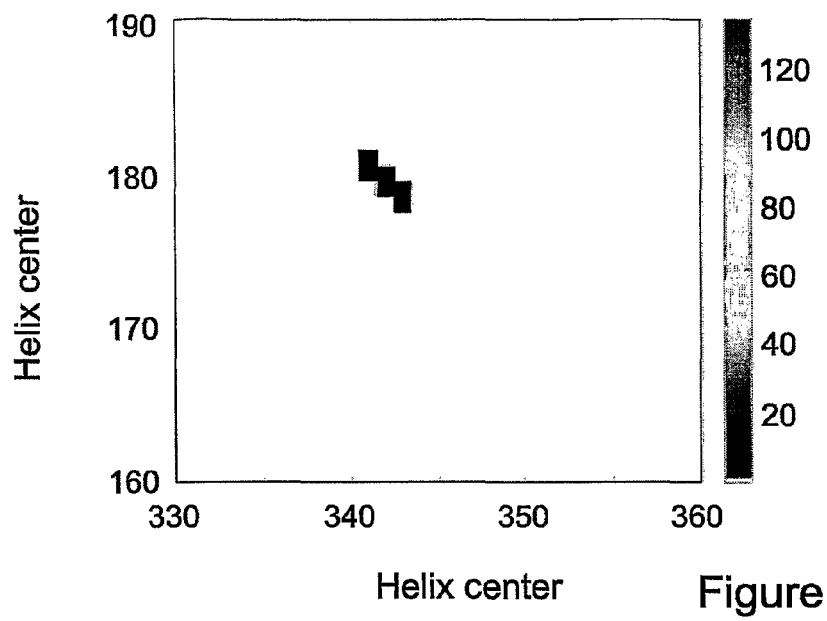
FIG. 8A shows a zoomed-in view of the most prominent parallel helix-helix signal of clusterin, which appears in FIG. 7D.
Figure 8B:
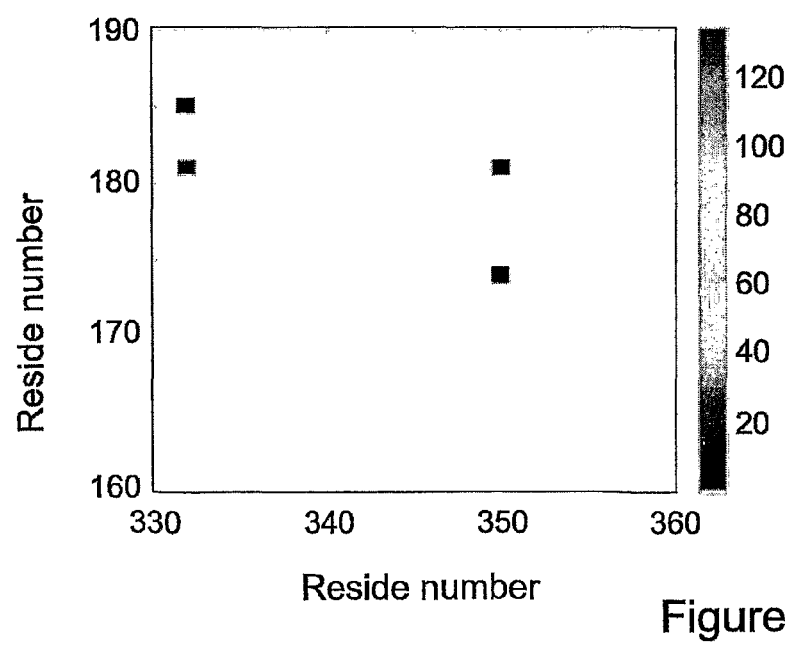
FIG. 8B shows a zoomed in view of the corresponding residue-residue contact map, which appears in FIG. 7C.

FIGS. 8A-8D present *In Silico* detection of a helix-helix interaction in clusterin. FIG. 8A shows a zoomed in view of the most prominent parallel helix-helix signal of clusterin, which appeared in FIG. 7D. FIG. 8B shows a zoomed in view of the corresponding residue-residue contact map, which appeared in FIG. 7C.

Example 7

Analysis of CGEN-CL1 Binding to Recombinant Clusterin

The capability of CGEN-CL1 to specifically bind to recombinant Clusterin protein was investigated using the BIACORE technology, measuring protein-protein interaction and binding affinity. The technology is based on surface plasmon resonance (SPR), an optical phenomenon that enables detection of unlabeled interactants in real time. The SPR-based biosensors can be used in determination of active concentration, screening and characterization in terms of both affinity and kinetics.

Peptide-protein interaction was analyzed using surface plasmon resonance. Analysis of the interaction between CGEN-CL1 [SEQ ID NO:1] and recombinant human clusterin (Biovendor, Modrice, Czech republic cat no: RD172034100) was conducted using the BIAcore biosensor (Pharmacia Biosensor, Uppsala, Sweden). Clusterin was immobilized directly to a CM5 sensor chip (2000 resonance units (RU)). Solution containing five different concentrations of CGEN-CL1 [SEQ ID NO:1] (312, 625, 1250, 2500 and 5000 nM) was injected into the sample chamber of the BIACORE device and the interaction was monitored for 5 minutes using surface plasmon resonance.

As a background, the solutions were also injected onto an empty flow cell with no immobilized ligand and the binding levels achieved were subtracted. Data were analyzed using BIAevaluation software.

Figure 9:
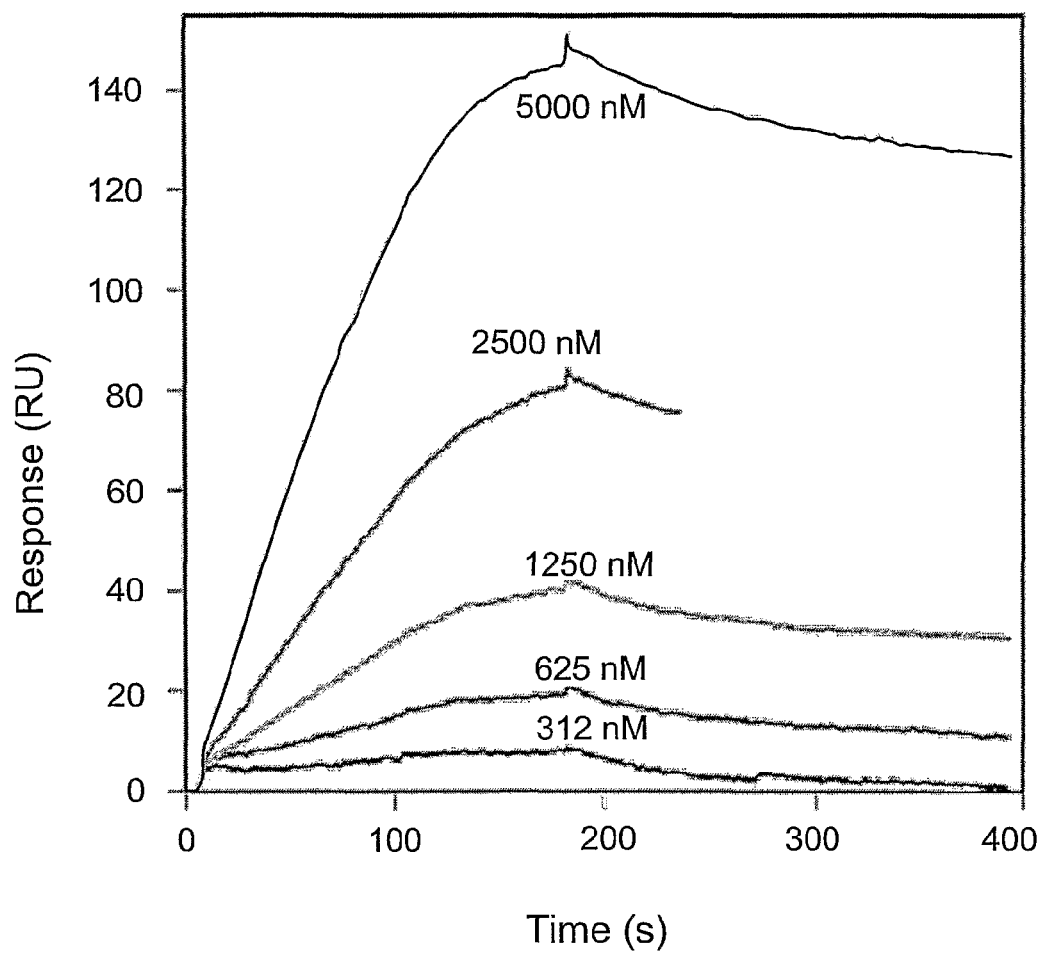
FIG. 9 presents the results of analysis of the interaction of different concentrations (marked) of CGEN-CL1 with its parent protein Clusterin.

FIG. 9 presents the results of the analysis of the interaction of CGEN-CL1 with its parent protein clusterin and shows that CGEN-CL1 binds to its parent protein clusterin in a dose dependent manner. Significant binding is detected from 0.5 to 5

Example 8

Biological Confirmation for the Computationally Identified Interaction Between CGEN-CL1 (SEQ ID NO: 1) and its Helix Partner (SEQ ID NO: 5)

In order to evaluate whether the two computationally identified α-helices (CGEN-CL1 (SEQ ID NO: 1) and its helix partner (SEQ ID NO: 5)) bind to each other in the Clusterin protein, a co-incubation of the two peptides was analyzed for its ability to eliminate the biological activity of CGEN-CL1.

Pre-incubation for 30 minutes of 150 nM CGEN-CL1 peptide (SEQ ID NO:1) with an equimolar concentration of the helix partner (SEQ ID NO:5) was carried out at room temperature. CGEN-CL1 peptide (SEQ ID NO:1) alone, or the helix partner (SEQ ID NO:5) alone or the pre-incubated CGEN-CL1 peptide (SEQ ID NO:1) with helix partner (SEQ ID NO:5) were used for viability assay of A549 cells, using MTT assay as described in Example 2 herein.

Figure 10B:
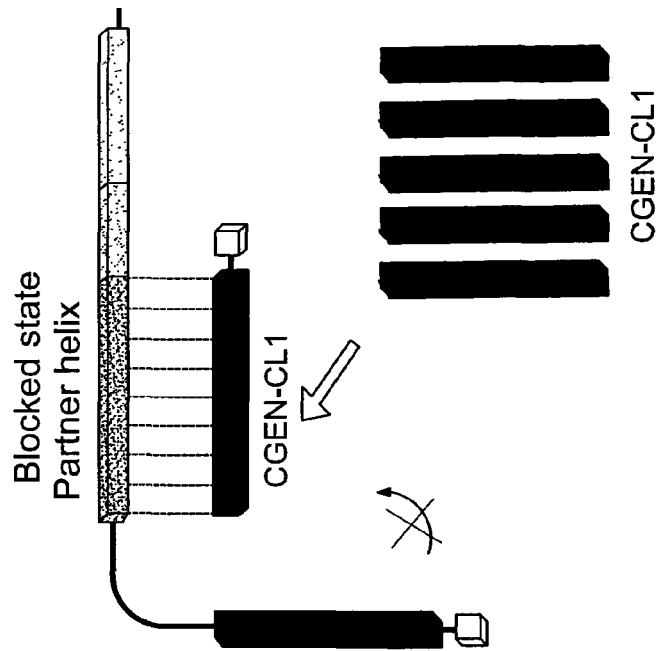
FIGS. 10A-10C present, without being bound by theory, a potential mechanism of action of CGEN-CL1.
Figure 10A:
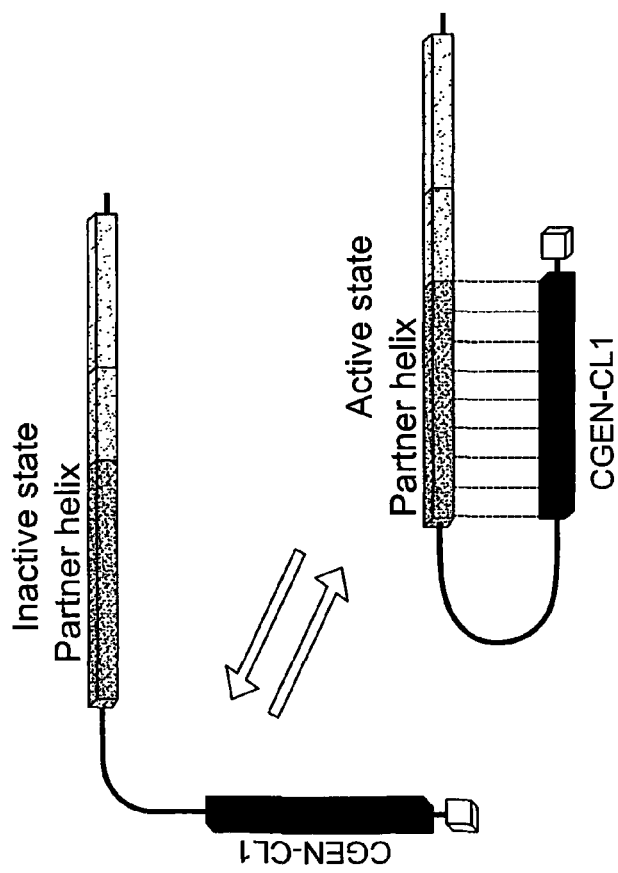
Figure 10C:
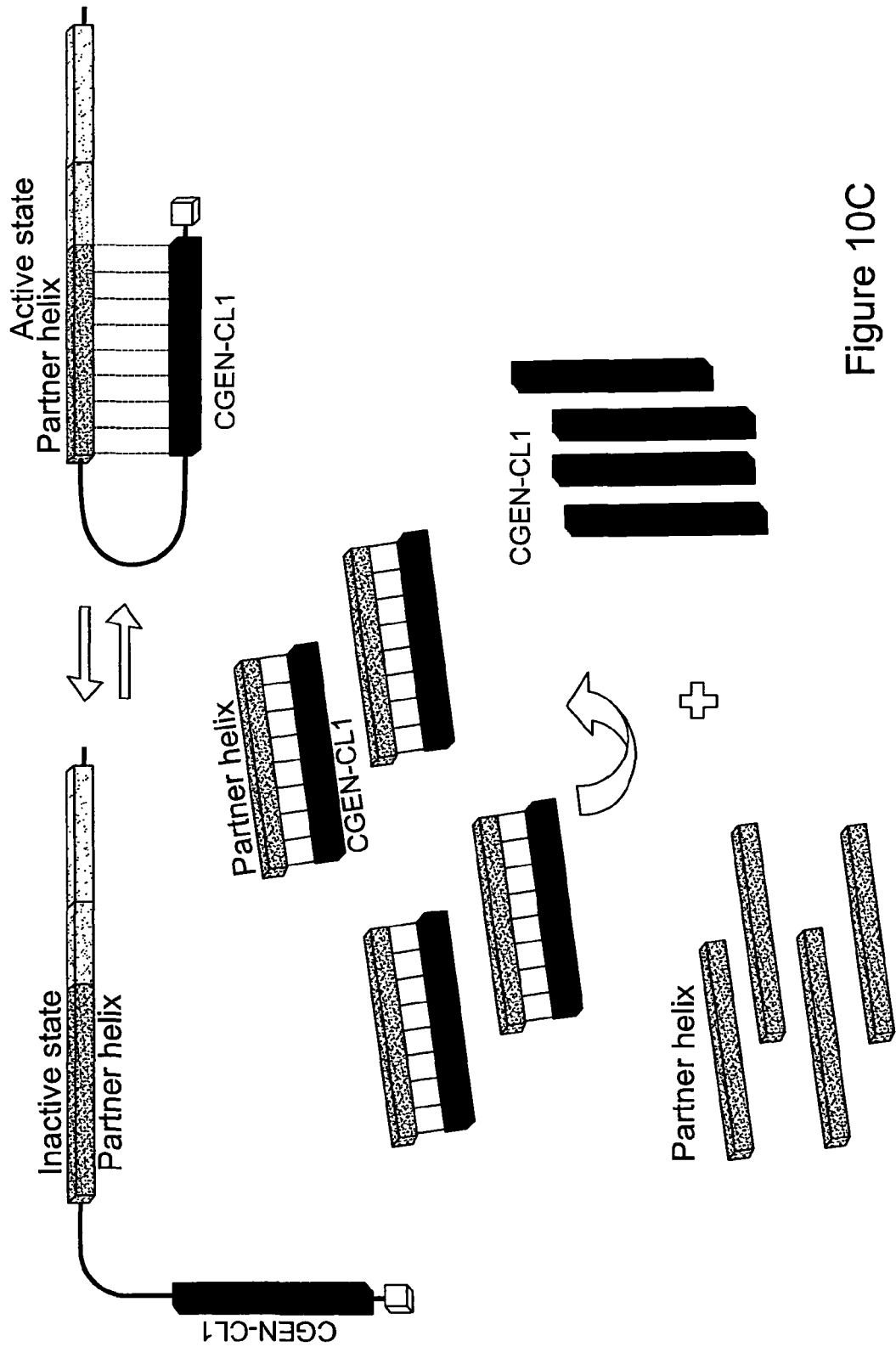

FIGS. 10A-10C present a potential mechanism of action of CGEN-CL1. FIG. 10A presents a schematic diagram of a conformational change in a protein, and FIG. 10B shows the blockage of the conformational change in a protein by a peptide corresponding to one of the helices. FIG. 10C demonstrates that according to this potential mechanism of action, pre-incubation of the blocking peptide CGEN-CL1 (SEQ ID NO: 1) with a peptide corresponding to a partner helix (SEQ ID NO:5) abolishes the inhibitory effect of CGEN-CL1 (SEQ ID NO: 1).

Figure 11A:
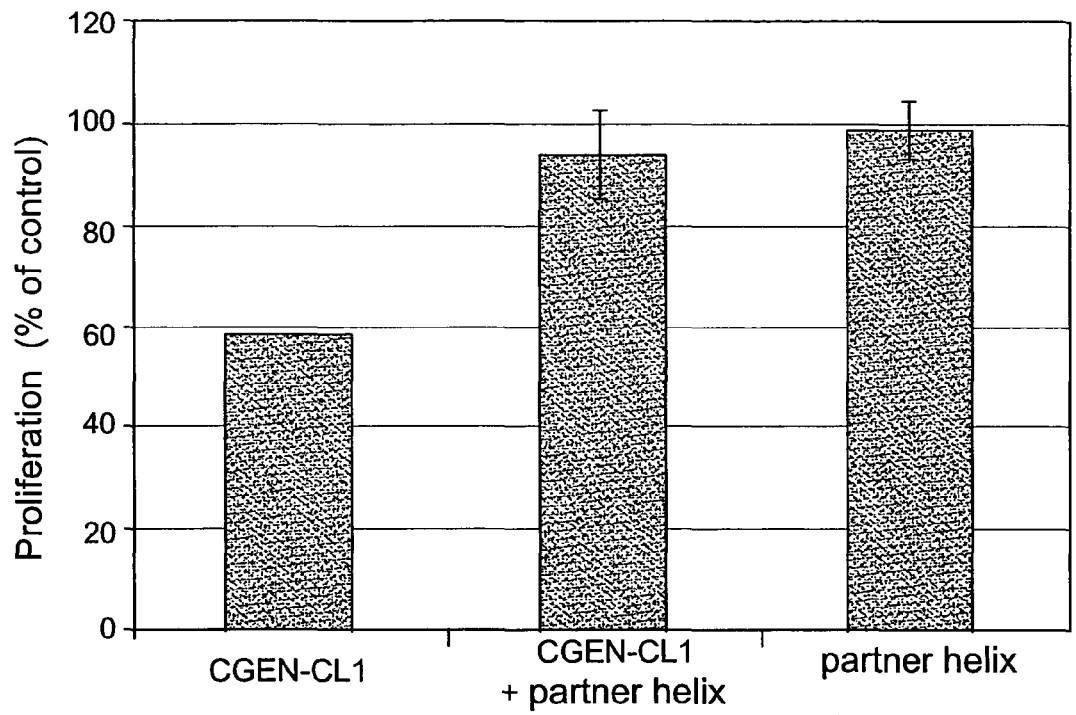
FIG. 11A demonstrates the effect of CGEN-CL1 (SEQ ID NO:1) alone (left bar); counterpart helix peptide (SEQ ID NO:5) alone (right bar); and a combination of CGEN-CL1 (SEQ ID NO:1) with SEQ ID NO:5 preincubated for 30 min at room temperature (central bar) on cell growth of A549 cancer cell lines as revealed by MTT assay.

The experimental data were consistent with the computationally predicted mode of action, in which the biological inhibitory activity of the peptides takes place upon their binding to the segment corresponding to the counterpart helix within the parent protein (FIG. 11A). Indeed, these results support the existence of both an active ("close") conformation, in which the two segments interact with each other, and an inactive ("open") conformation, in which the two segments do not interact (FIG. 11A).

FIG. 11A presents the results of pre-incubation of 150 nM CGEN-CL1 peptide (SEQ ID NO:1) with an equimolar concentration of a peptide corresponding to its counterpart helix (SEQ ID NO:5), leading to attenuated the activity of CGEN-CL1.

As shown in FIG. 11A, the biological effect of CGEN-CL1 (SEQ ID NO:1), that was demonstrated herein in FIGS. 1C and 1D, was abolished in the presence of partner helix peptide (SEQ ID NO:5).

Example 9

Co-Incubation of CGEN-CL1 with a Partner Helix Blocks its Binding to Parent Protein Clusterin Peptide-protein interaction was analyzed using surface plasmon resonance. Analysis of the interaction between CGEN-CL1 [SEQ ID NO:1] and recombinant human clusterin (Biovendor, Modrice, Czech republic cat no:

RD172034100) was conducted using the BIAcore biosensor (Pharmacia Biosensor, Uppsala, Sweden). Clusterin was immobilized directly to a CM5 sensor chip (2000 resonance units (RU)). Solution containing either 10 µM of CGEN-CL1 [SEQ ID NO:1] peptide or a mixture of CGEN-CL1 and its partner helix (SEQ ID NO:5), 10 µM each, preincubated for 30 minutes at room temperature, was injected to the BIAcore. As a background, the solutions were also injected onto an empty flow cell with no immobilized ligand and the binding levels achieved were subtracted. Data was analyzed using BIAevaluation software.

Figure 11B:
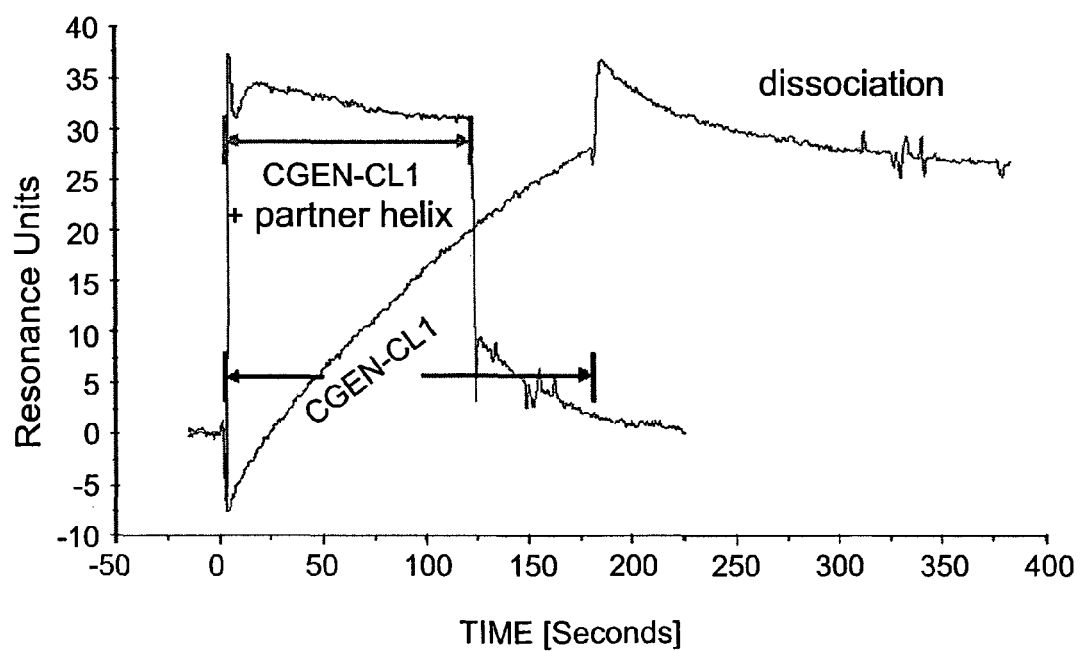
FIG. 11B demonstrates the effect of the co-incubation of CGEN-CL1 (SEQ ID NO:1) with a partner helix (SEQ ID NO: 5) on CGEN-CL1 binding to the parent clusterin protein.

As demonstrated in FIG. 11B, the co-incubation of CGEN-CL1 (SEQ ID NO:1) with its partner helix (SEQ ID NO: 5) completely abolished the binding of CGEN-CL1 to recombinant Clusterin.

Example 10

Antibodies

Reagents other than peptides are also used to inhibit the formation of the helix-helix interactions between the segment corresponding to residues 150-170 and the segment corresponding to residues 336-357. Antibodies that specifically bind to an epitope in a helix partner peptide of CGEN-CL1 or an epitope in the segment corresponding to CGEN-CL1 itself are highly effective to inhibit the formation of the helix-helix interactions between the segment corresponding to residues 150-170 and the segment corresponding to residues 336-357, and thereby to act as antagonists of clusterin.

Figure 12:
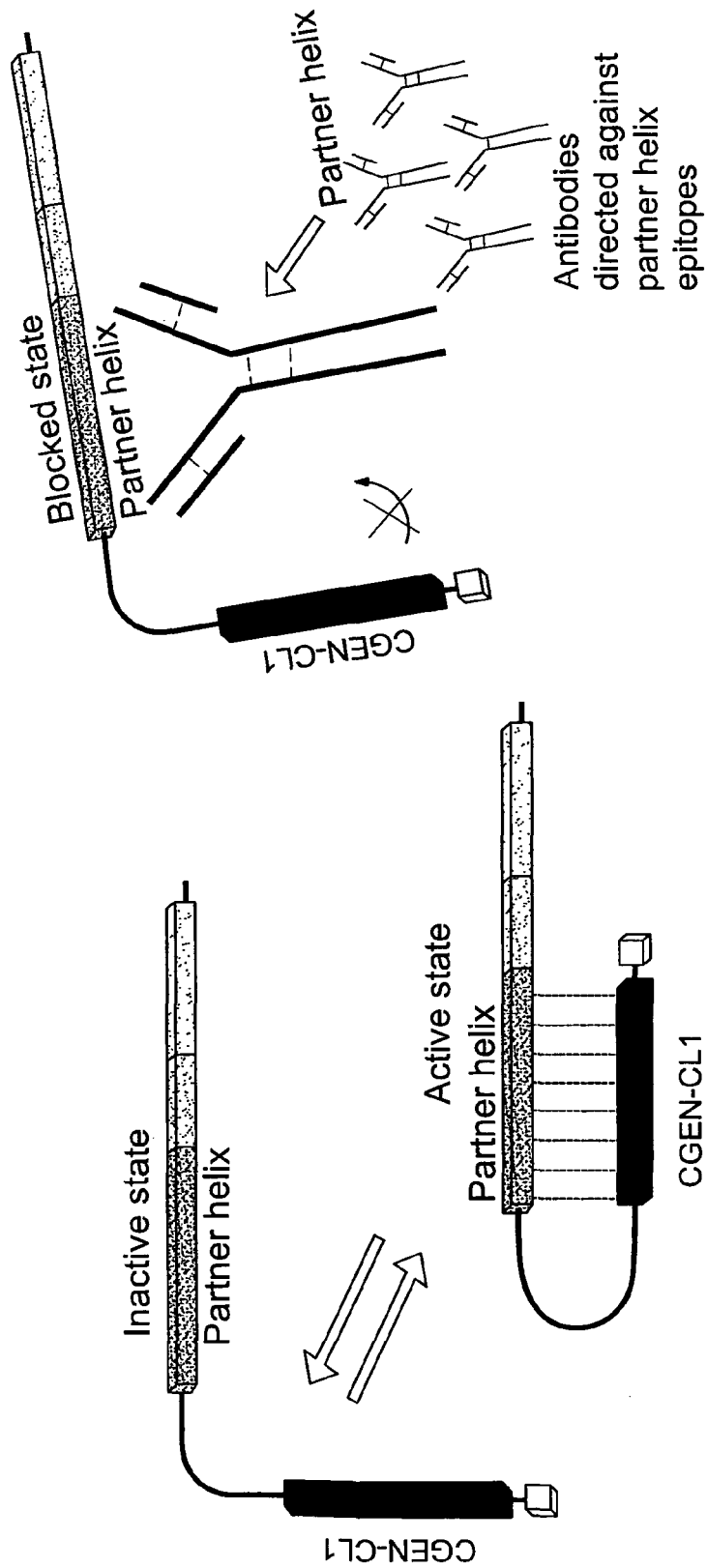
FIG. 12 shows a schematic drawing demonstrating that antibodies aimed against an epitope derived from a helix partner have the capability to block helix-helix interaction within the clusterin protein and thereby cause a biological effect resembling the biological activity achieved by CGEN-CL1.

FIG. 12 shows a schematic drawing demonstrating that antibodies aimed against an epitope derived from a helix partner have the capability to block the helix-helix interaction within the clusterin protein and thereby cause a biological effect resembling the biological activity achieved by CGEN-CL1.

Thus, antibodies that specifically bind to an epitope in a helix partner peptide of CGEN-CL1 or an epitope in the segment corresponding to CGEN-CL1 or homologs or fragments thereof are used for treating wide range of conditions, disorders and diseases, selected from but not limited to cancer, neurodegenerative disease, disease related to inflammation of the gastrointestinal tract, pathological disorder characterized by increased oxidative stress, cardiovascular disease, eye disorder, kidney degeneration disorder, and pancreatic disorder.

Example 11

Orthologs

The sequence of the CGEN-CL1 (SEQ ID NO: 1), corresponding to amino acid residues 150-170, in the human gi|42740907 protein (SEQ ID NO: 14) is highly conserved throughout other species and orthologs, as can be seen from FIG. 13.

FIG. 13 shows a multiple alignment comparison of the sequence of CGEN-CL1 (SEQ ID NO:1) and the homologous sequences derived from >gi|126723644_0|*[Oryctolagus cuniculus]*, >gi|126352584_0|*[Equus caballus]*, >gi|4752277_0|*[Sus scrofa]*, >gi|50979240_0|*[Canis familiaris]*, >gi|461756_0|*[Rattus norvegicus]*, >gi|27806907_0|*[Bos taurus]*, >gi|1705937_0|*[Coturnix coturnix japonica]*, >gi|729152_0|*[Mus musculus]*, corresponding to SEQ ID NOs: 6-13.

The invention claimed is:

1. An isolated peptide consisting of an amino acid sequence as set forth in any one of SEQ ID NOs: 1, 3, 6, 7, 8, 10, 11, and 12.

2. A fusion protein comprising a peptide of claim 1.

3. A pharmaceutical composition, comprising:
a peptide according to claim 1,
a fusion protein comprising the peptide, and a pharmaceutically acceptable carrier.

4. A method of treating a cancer comprising clusterin-expressing cancer cells comprising administering a pharmaceutically effective amount of a peptide according to claim 1, a fusion protein comprising the peptide, a pharmaceutical composition comprising the peptide, and a pharmaceutically acceptable carrier to a subject in need thereof, wherein the peptide or the fusion protein or the pharmaceutical composition is administered alone or in combination with another therapeutic agent.

5. A method according to claim 4, wherein the cancer is selected from the group consisting of breast cancer, prostate cancer, lung cancer, colorectal cancer, melanoma, renal cancer, bladder cancer and pancreatic cancer.

6. A method of inhibiting the epithelial-to-mesenchymal transition in carcinoma cells comprising administering a pharmaceutically effective amount of a peptide according to claim 1, a fusion protein comprising the peptide, a pharmaceutical composition comprising the peptide, and a pharmaceutically acceptable carrier to a subject in need thereof, wherein the peptide or the fusion protein or the pharmaceutical composition is administered alone or in combination with another therapeutic agent.

* * * * *

SEQUENCE LISTING

```
<160> NUMBER OF SEQ ID NOS: 16

<210> SEQ ID NO 1
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 1

Phe Tyr Phe Trp Met Asn Gly Asp Arg Ile Asp Ser Leu Leu Glu Asn
1               5                   10                  15

Asp Arg Gln Gln Thr
            20

<210> SEQ ID NO 2
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 2
ttctacttct ggatgaatgg tgaccgcatc gactccctgc tggagaacga ccggcagcag      60
acg                                                                   63

<210> SEQ ID NO 3
<211> LENGTH: 41
<212> TYPE: PRT
```

```
<213> ORGANISM: Artificial Sequence
<220> FEATURE:
<223> OTHER INFORMATION: Synthetic polypeptide

<400> SEQUENCE: 3

Leu Glu Glu Phe Leu Asn Gln Ser Ser Pro Phe Tyr Phe Trp Met Asn
1               5                   10                  15

Gly Asp Arg Ile Asp Ser Leu Leu Glu Asn Asp Arg Gln Gln Thr His
            20                  25                  30

Met Leu Asp Val Met Gln Asp His Phe
        35                  40

<210> SEQ ID NO 4
<211> LENGTH: 123
<212> TYPE: DNA
<213> ORGANISM: Artificial Sequence
<220> FEATURE:
<223> OTHER INFORMATION: Synthetic polynucleotide

<400> SEQUENCE: 4
cttgaggagt tcctgaacca gagctcgccc ttctacttct ggatgaatgg tgaccgcatc     60
gactccctgc tggagaacga ccggcagcag acgcacatgc tggatgtcat gcaggaccac    120
ttc                                                                  123

<210> SEQ ID NO 5
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 5

Arg Leu Thr Arg Lys Tyr Asn Glu Leu Leu Lys Ser Tyr Gln Trp Lys
1               5                   10                  15

Met Leu Asn Thr Ser Ser
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 6

Phe Tyr Phe Trp Ile Asn Gly Asp Arg Ile Asp Ser Leu Leu Glu Asn
1               5                   10                  15

Asp Arg Gln Gln Ser
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 7

Phe Tyr Phe Trp Ile Asn Gly Asp Arg Ile Asp Ser Leu Leu Glu Asn
1               5                   10                  15

Asp Arg Gln Gln Thr
            20
```

```
<210> SEQ ID NO 8
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 8

Phe Tyr Phe Trp Ile Asn Gly Asp Arg Ile Asp Ser Leu Met Glu Asn
1               5                   10                  15

Asp Arg Gln Gln Ser
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 9

Phe Tyr Phe Trp Met Asn Gly Asp Arg Ile Asp Ser Leu Leu Glu Asn
1               5                   10                  15

Asp Arg Gln Gln Thr
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 10

Phe Tyr Phe Trp Met Asn Gly Asp Arg Ile Asp Ser Leu Leu Glu Ser
1               5                   10                  15

Asp Arg Gln Gln Ser
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 11

Phe Tyr Phe Trp Ile Asn Gly Asp Arg Ile Asp Ser Leu Met Glu Asn
1               5                   10                  15

Asp Arg Glu Gln Ser
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 12

Phe Ser Ile Trp Val Asn Gly Glu Arg Ile Asp Leu Leu Asp Arg
1               5                   10                  15

Glu Gln Arg Gln Glu
            20
```

```
<210> SEQ ID NO 13
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 13

Phe Tyr Phe Trp Met Asn Gly Asp Arg Ile Asp Ser Leu Leu Glu Ser
1               5                   10                  15

Asp Arg Gln Gln Ser
            20

<210> SEQ ID NO 14
<211> LENGTH: 449
<212> TYPE: PRT
<213> ORGANISM: Homo sapiens

<400> SEQUENCE: 14

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300
```

```
                                                        -continued

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
            325                 330                 335

Leu Thr Arg Lys Tyr Asn Glu Leu Leu Lys Ser Tyr Gln Trp Lys Met
        340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
        370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
            405                 410                 415

Val Thr Val Pro Val Glu Val Ser Arg Lys Asn Pro Lys Phe Met Glu
        420                 425                 430

Thr Val Ala Glu Lys Ala Leu Gln Glu Tyr Arg Lys Lys His Arg Glu
            435                 440                 445

Glu

<210> SEQ ID NO 15
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 15

Glu Leu Asp Glu Ser Leu Gln Val Ala Glu Arg Leu Thr Arg Lys Tyr
1               5                   10                  15

Asn Glu Leu Leu Lys Ser Tyr Gln Trp Lys Met Leu Asn Thr Ser Ser
            20                  25                  30

Leu Leu Glu Gln Leu Asn Glu Gln Phe Asn
        35                  40

<210> SEQ ID NO 16
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 16

Asn Asn Pro Ser Gln Ala Lys Leu Arg Arg Glu Leu Asp Glu Ser Leu
1               5                   10                  15

Gln Val Ala Glu Arg Leu Thr Arg Lys Tyr Asn Glu Leu Leu Lys Ser
            20                  25                  30

Tyr Gln Trp Lys Met Leu Asn Thr Ser Ser Leu Leu Glu Gln Leu Asn
        35                  40                  45

Glu Gln Phe Asn Trp Val Ser Arg Leu Ala Asn Leu Thr Gln
    50                  55                  60
```